US011826311B2

(12) United States Patent
Huang et al.

(10) Patent No.: US 11,826,311 B2
(45) Date of Patent: Nov. 28, 2023

(54) COAXIAL NOZZLE CONFIGURATION AND METHODS THEREOF

(71) Applicant: University of Florida Research Foundation, Inc., Gainesville, FL (US)

(72) Inventors: Yong Huang, Gainesville, FL (US); Yifei Jin, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 135 days.

(21) Appl. No.: 17/230,527

(22) Filed: Apr. 14, 2021

(65) Prior Publication Data

US 2021/0236386 A1 Aug. 5, 2021

Related U.S. Application Data

(62) Division of application No. 16/001,386, filed on Jun. 6, 2018, now abandoned.

(60) Provisional application No. 62/517,329, filed on Jun. 9, 2017.

(51) Int. Cl.
| | |
|---|---|
| *A61J 3/07* | (2006.01) |
| *B65D 81/32* | (2006.01) |
| *B05B 1/30* | (2006.01) |
| *A61K 9/48* | (2006.01) |
| *A23P 30/25* | (2016.01) |

(52) U.S. Cl.
CPC ............ *A61J 3/074* (2013.01); *A61J 3/07* (2013.01); *A61K 9/4808* (2013.01); *B05B 1/3086* (2013.01); *A23P 30/25* (2016.08); *B65D 81/3216* (2013.01)

(58) Field of Classification Search
CPC .... A61J 3/07; A61J 3/071; A61J 3/072; A61J 3/075; A61J 3/077; B65D 81/3216; B65D 81/3222; B65D 81/3227
USPC .............................................................. 425/5
See application file for complete search history.

(56) References Cited

U.S. PATENT DOCUMENTS

| | | | |
|---|---|---|---|
| 2,339,114 A | 1/1944 | Scherer | |
| 2,766,478 A * | 10/1956 | Raley, Jr. ................. | A61J 3/07 264/DIG. 37 |
| 2,911,672 A * | 11/1959 | Van Erven ................ | A61J 3/07 264/DIG. 37 |
| 4,251,195 A | 2/1981 | Suzuki et al. | |
| 4,422,985 A | 12/1983 | Morishita et al. | |
| 4,695,466 A | 9/1987 | Morishita et al. | |
| 4,888,140 A * | 12/1989 | Schlameus ................ | A61J 3/07 264/4.4 |

(Continued)

OTHER PUBLICATIONS

Cory Berkland et al, Monodisperse Liquid-filled Biodegradable Microcapsules, May 2007, Pharmaceutical Research, vol. 24, No. 5, pp. 1007-1013 (Year: 2007).*

(Continued)

*Primary Examiner* — Seyed Masoud Malekzadeh
(74) *Attorney, Agent, or Firm* — ALSTON & BIRD LLP

(57) ABSTRACT

Embodiments of the present disclosure provide for coaxial nozzles, capsule fabrication systems comprising coaxial nozzles, and methods of capsule fabrication using capsule fabrication systems. In certain embodiments, coaxial nozzle configurations, capsule fabrication systems, and methods as described herein can be used for multi-layered capsule fabrication.

19 Claims, 18 Drawing Sheets

(56) References Cited

U.S. PATENT DOCUMENTS

| | | | |
|---|---|---|---|
| 5,125,812 A | 6/1992 | Held | |
| 5,209,978 A * | 5/1993 | Kosaka | A61J 3/07 |
| | | | 264/4.4 |
| 5,230,207 A | 7/1993 | Hartzell et al. | |
| 5,232,712 A | 8/1993 | Mills et al. | |
| 5,888,538 A | 3/1999 | Kiefer et al. | |
| 6,174,466 B1 * | 1/2001 | Kiefer | B01J 13/04 |
| | | | 264/4.4 |
| 8,506,273 B2 | 8/2013 | Ikeda et al. | |
| 2006/0096252 A1 | 5/2006 | Nakamura | |
| 2021/0236386 A1 * | 8/2021 | Huang | A61K 9/4808 |

OTHER PUBLICATIONS

Christoph Heinzen, et al., "Use of Vibration Technology for Jet Break—Up for Encapsulation of Cells, Microbes and Liquids in Monodisperse Microcapsules", ResearchGate—https://www.researchgate.net/publication/228747123, Jan. 2004, 1-17.

Rui Yao, et al., "Injectable cell/hydrogel microspheres induce the formation of fat lobule-like microtissues and vascularized adipose tissue regeneration", Biofabrication 4(2012) 045003, 1-10.

Cory Berkland, et al., "Monodisperse Liquid-filled Biodegradable Microcapsules", Pharmaceutical Research, 24(5), May 2007, 1007-1013.

* cited by examiner

FIG. 2A
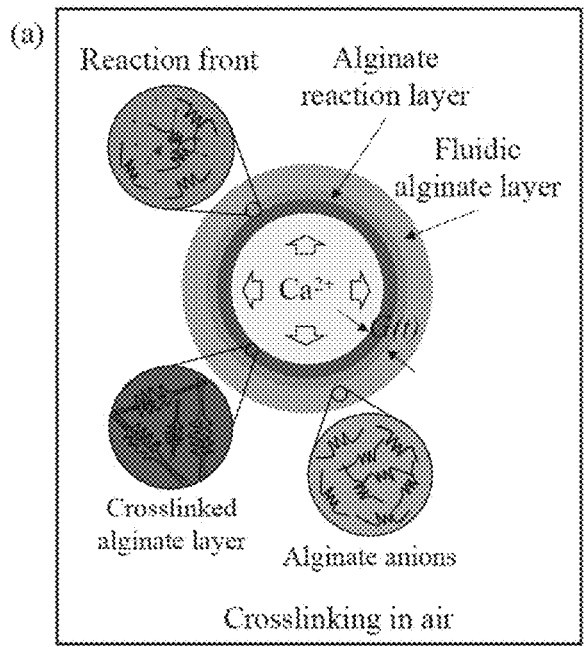
FIG. 2B
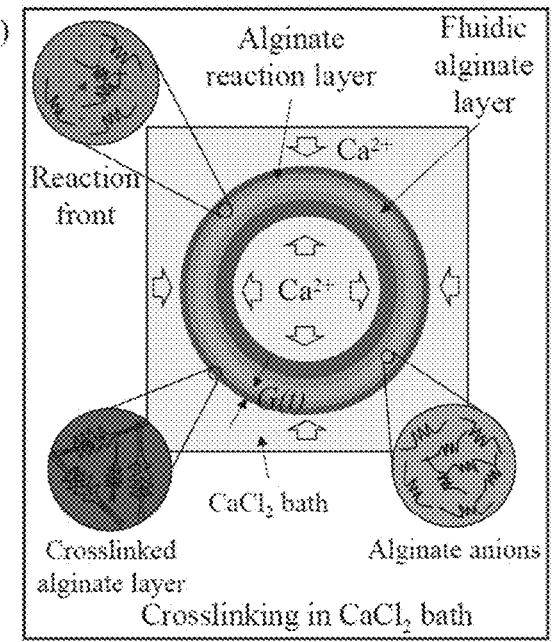
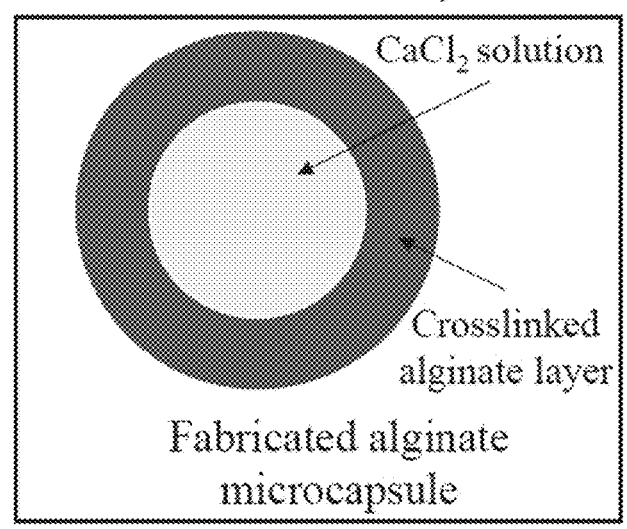
FIG. 2C (a)

(b)

Table 1. Physical and rheological properties

| Sodium alginate (w/v) | Density $\rho$ (kg/m$^3$) | Viscosity $\eta_0$ (mPa·s) | Surface tension (mN/m) |
|---|---|---|---|
| 1.0% | 1010 | 31.1 | 47.5 |
| 2.0% | 1020 | 139.5 | 44.6 |

FIG. 7

Table 2. Levels and factors of the annular and sheath channels

| Factor | A | B | C | D |
|---|---|---|---|---|
| Annular channel | D (mm)<br>7.50, 8.00, 8.50 | $L_1$ (mm)<br>2.00, 3.00, 4.00 | $L_2$ (mm)<br>12.50, 12.75, 13.00 | $L_3$ (mm)<br>2.00, 2.25, 2.50 |
| Sheath channel | L (mm)<br>1.50, 1.75, 2.00 | $D_1$ (mm)<br>14.00, 15.00, 16.00 | $D_2$ (mm)<br>11.00, 12.00, 13.00 | H (mm)<br>8.00, 8.28, 8.56 |

FIG. 8

| 10 | Copper Gasket |
| 9 | Copper Gasket |
| 8 | Bolt |
| 7 | Die |
| 6 | Medium |
| 5 | Collar B |
| 4 | Sol Supplier |
| 3 | Set Screw |
| 2 | Mandrel |
| 1 | Collar A |

Table 3. Design and simulation results of orthogonal experiments

FIG. 23

COAXIAL NOZZLE CONFIGURATION AND METHODS THEREOF

CLAIM OF PRIORITY TO RELATED APPLICATIONS

This application is a divisional application claiming priority to, and the benefit of, co-pending U.S. patent application Ser. No. 16/001,386, filed on Jun. 6, 2018, now is abandoned which claims priority to, and the benefit of, U.S. provisional application entitled "COAXIAL NOZZLE CONFIGURATION AND METHODS THEREOF" having Ser. No. 62/517,329, filed on Jun. 9, 2017, all of which are hereby incorporated by reference herein in their entireties.

STATEMENT OF GOVERNMENTAL SUPPORT

This invention was made with government support under grant number 1314834 awarded by the National Science Foundation. The government has certain rights in the invention.

BACKGROUND

Encapsulation is a process involving the complete envelopment of preselected core material with a well-defined porous or impermeable membrane. Encapsulation has been of great importance in recent years and has been widely used in many fields including pharmaceutical, chemical, and food industries, as well as in various applications related to agriculture, biotechnology, and medicine, to name a few. The main purpose of encapsulation is to immobilize, protect, and control the release of entrapped materials such as flavor, living cells, and pharmaceutical compounds.

Multi-layered encapsulation has been of great interest for various pharmaceutical, chemical and food industries and confers advantages over single-layered encapsulation. Fabrication of well-defined capsules with more than one shell layer still poses a significant fabrication challenge, however. As a result, current techniques are not as effective as desired, and there is a need to overcome deficiencies in current fabrication techniques.

SUMMARY

Embodiments of the present disclosure provide for a coaxial nozzle, which can comprise a core channel, an annular channel, and a sheath channel. The nozzle can further comprise one or more outlet nozzles. The core channel, the annular channel, and the sheath channel of the nozzle each can further comprise an inlet configured to receive fluid.

Embodiments of the present disclosure provide for a capsule fabrication system comprising a coaxial nozzle. The coaxial nozzle can comprise a core channel, an annular channel, and a sheath channel, and can be configured to output one or more capsules into a collection bath. Capsule fabrication systems as described herein can further comprise a vibrator attached to or in physical communication with the coaxial nozzle.

Capsule fabrication systems as described herein can further comprise a fluid delivery system configured to deliver fluids to one or more of the core channel, the annular channel, and the sheath channel.

One or more capsules outputted by the capsule fabrication system can be one or more multi-layered capsules.

Described herein are methods for capsule fabrication. Methods for capsule fabrication as described herein can comprise: presenting a capsule fabrication system, comprising a coaxial nozzle, with a core channel, an annular channel, and a sheath channel, and configured to output one or more capsules; wherein the core channel, the annular channel, and the sheath channel each further comprise an inlet configured to receive fluid; and a collection bath configured to receive one or more capsules from the coaxial nozzle; initiating capsule fabrication, comprising delivering fluid to one or more of the core channel, the annular channel, and the sheath channel of the capsule fabrication system; forming a compound flow from the fluid delivered to the one or more channels, wherein the compound flow comprises one or more of a core flow, an annular flow, and a sheath flow; introducing a vibration to the compound flow, developing the one or more capsules; introducing the one or more capsules to a collection bath comprising a crosslinking agent; and crosslinking the one or more capsules to form one or more stabilized capsules.

Capsule fabrication systems of methods described herein can further comprise a fluid delivery system. One or more capsules or one or more stabilized capsules created by methods as described herein can be multi-layered capsules. Multi-layered capsules created by methods as described herein can have a core-shell-shell structure. Crosslinking agents of methods and systems as described herein can be $Ca^{2+}$. Fluids as described herein can comprise alginate. Fluids as described herein can comprise $CaCl_2$. Fluids delivered to the annular channel, the sheath channel, or both in methods described herein can be the same or can be different for each respective channel. Multi-layered capsules formed by systems and methods herein can have a core-shell-shell structure.

Other devices, methods, features, and advantages will be, or become, apparent to one with skill in the art upon examination of the following drawings and detailed descriptions. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure.

FIGS. 2A-2C illustrate a schematic of alginate crosslinking process with the presence of calcium cations. FIG. 2A is an embodiment of a schematic of alginate solution being crosslinked in air; FIG. 2B is an embodiment of a schematic of entire alginate capsule being crosslinked in a calcium chloride ($CaCl_2$) bath; and FIG. 2C depicts an embodiment of a fabricated alginate capsule (note only one layer is shown for illustration in FIG. 2C).

FIG. 3A is a schematic of an embodiment of a nozzle assembly. FIG. 3B shows the structure dimensions of the annular channel of the nozzle assembly of FIGS. 3A and 3C shows the structure dimensions of the sheath channel of the nozzle assembly of FIG. 3A. FIG. 3D demonstrates points selected to evaluate the velocity uniformity in the channels, and typical simulation results of the velocity distribution of the annular flow and the sheath flow at the outlet of the nozzle are shown in FIGS. 3E and 3F respectively.

FIG. 4A is a schematic of the three-layered coaxial nozzle structure. The velocity field of alginate solution flowing in the annular channel and the sheath channel are shown in FIGS. 4B and 4C, respectively. FIG. 4D depicts the assembly of the assembled three-layered coaxial nozzle (scale bar 4.0 mm), and FIG. 4E shows the view of its nozzle outlets (scale bars 4.0 mm for FIG. 4E and 0.5 mm for the inset of FIG. 4E). The inner set, middle set, and outer set of the three-layered coaxial nozzle are shown in FIGS. 4F, 4G, and 4H, respectively. The scale bars in FIGS. 4F and 4G are 1.0 mm and the scale bar in FIG. 4H is 2.0 mm.

FIG. 6A shows capsule and core diameters as a function of core flow rate; FIG. 6B shows inner and outer shell layer thicknesses as a function of core flow rate; FIG. 6C depicts capsule and core diameters as a function of annular flow rate; FIG. 6D shows inner and outer shell layer thicknesses as a function of annular flow rate; FIG. 6E shows capsule and core diameters as a function of sheath flow rate; and FIG. 6F shows inner and outer shell layer thicknesses as a function of sheath flow rate. The graphs of FIG. 6 additionally show one standard deviation error bars and data points represent three samples.

FIG. 7 is a table showing physical and rheological properties of alginate solutions with different concentrations (1.0% and 2.0% (w/v)).

FIG. 8 is a table showing ranges of structural dimensions of the annular and sheath channels, as defined in FIGS. 3B and 3C respectively, according to the present disclosure.

FIG. 23 is a table that shows the design and simulation results of orthogonal experiments.

DETAILED DESCRIPTION

Figures 1A, 1B:
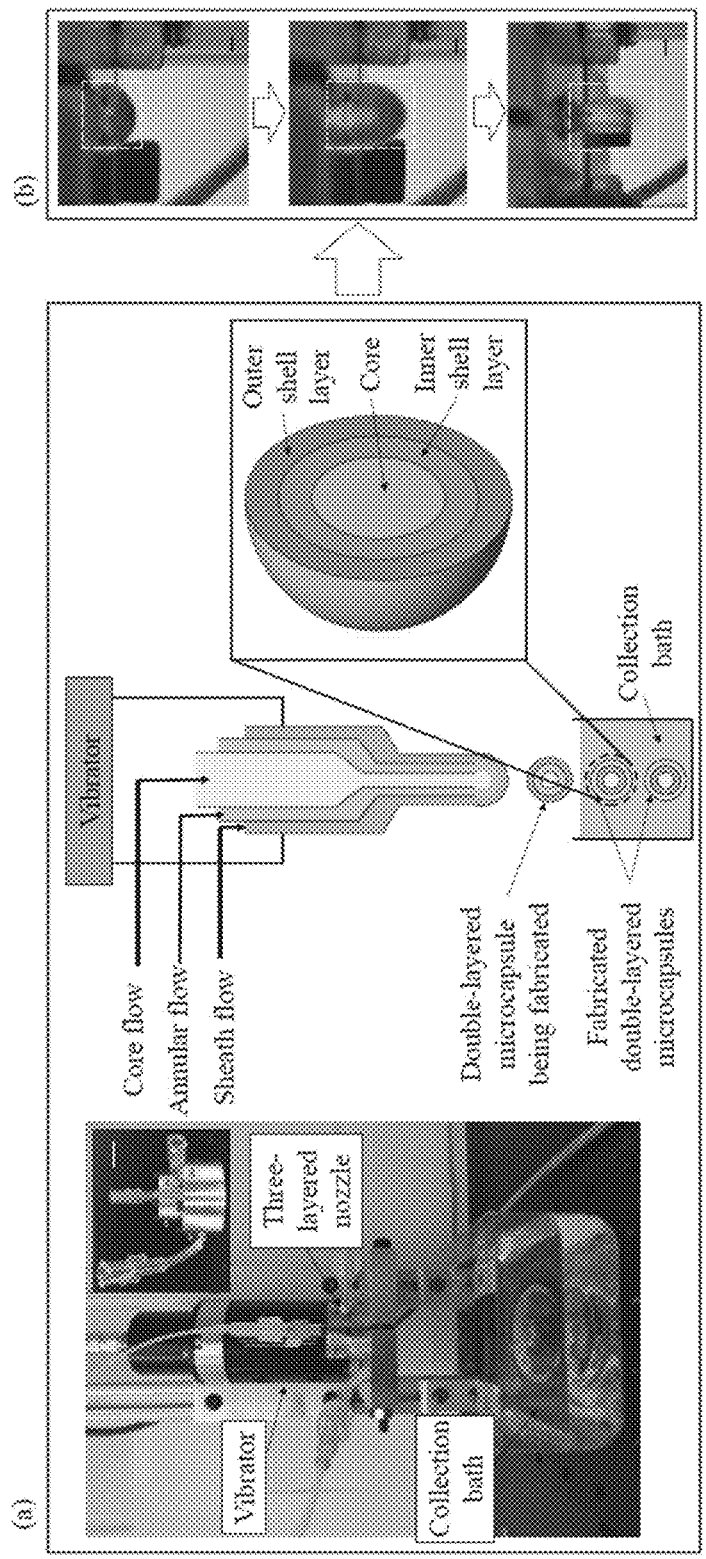
FIG. 1A shows a photograph and schematic of an embodiment of a multi-layered capsule fabrication system, more specifically a double-layered capsule fabrication system. The inset of the photograph shows an image of an embodiment of a three-layered coaxial nozzle (scale bar: 10 mm).
FIG. 1B is a series of photographs depicting methods as described herein. The photographic series shows an embodiment of a double-layered capsule being fabricated by the embodiment of the system of FIG. 1A.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of encapsulation, materials science, mechanical engineering, chemistry, food science, biotechnology, and the like. Such techniques are explained fully in the literature.

The following examples are put forth so as to provide those of ordinary skill in the art with a complete disclosure and description of how to perform the methods and use the compositions and compounds disclosed and claimed herein.

Efforts have been made to ensure accuracy with respect to numbers (e.g., amounts, temperature, etc.), but some errors and deviations should be accounted for. Unless indicated otherwise, parts are by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DISCUSSION

Embodiments of the present disclosure provide coaxial nozzles, capsule fabrication systems comprising coaxial nozzles, and methods thereof. Multi-layered encapsulation has been of great interest for various pharmaceutical, chemical and food industries. Fabrication of well-defined capsules with more than one shell layer still poses a significant fabrication challenge. Herein, multi-layered capsule fabrication systems comprising a coaxial nozzle to fabricate double-layered (core-shell-shell) capsules during vibration-assisted dripping are described, along with embodiments of coaxial nozzles and methods thereof.

During fabrication, different liquid materials can be dispensed through their corresponding channels of the coaxial nozzle to form a compound liquid flow, which comprises a core flow, an annular flow, and a sheath flow. A high frequency vibration is introduced to facilitate the breakup of the compound flow and the formation of double-layered capsules. Through applicable crosslinking mechanism(s) in a collection bath, capsules with a core-shell-shell structure can be fabricated.

For the fabrication of multi-layered capsules, various technologies have been studied, including compound or coaxial nozzle-based dripping/jetting, microdrop collision, and stirring/mixing-based bulk emulsification. During compound or coaxial nozzle-based fabrication, coaxial nozzles are used to produce the core droplet surrounded by a shell. When the flow rates of core and shell solutions increase, the droplet formation mechanism may change from dripping to jetting. A liquid core jet can be surrounded by an annular jet, which may be further surrounded by a carrier stream. For some applications, additional stimuli may be applied to facilitate the droplet formation process such as an electric field or vibration.

During microdrop collision, two inkjet nozzles are utilized to make droplets from different solutions such as aqueous and polymer solutions. After the collision of two inkjetted droplets, a polymer film is generated at the interface between two solutions due to the solvent exchange mechanism, and a compound droplet is fabricated with the polymer solution as the shell layer. During stirring/mixing-based bulk emulsification, two emulsification steps are typically adopted: a core material is stirred into a shell polymer solution, and the formed emulsion is further stirred into an emulsifier-based solution to form double-layered emulsions. The process can be improved by combining the co-nozzle extrusion with emulsification. By using a microcapillary device, the coaxial flow is formed at the exit of a tapered tube, and the outermost fluid is pumped through the outer coaxial region from the opposite direction; as the compound flow passes through the exit orifice, it ruptures into core-shell capsules. While this approach simplifies the two emulsification step-based conventional fabrication process, the outermost fluid is used to emulsify the coaxial flow into core-shell capsules instead of being a layer of the capsules. In addition, it is difficult to fabricate a double-layered coaxial glass microcapillary device as well as to control the formation of a three-layered compound flow in an emulsification flow. Thus, it is not practical to extend this approach to fabricate capsules with a well-defined core-shell-shell structure.

A purpose of encapsulation is to immobilize, protect, and control the release of entrapped materials such as flavor, living cells, and pharmaceutical compounds. The capsules fabricated by the fabrication system(s) described herein with well-defined porous or impermeable membranes can be used in many fields including pharmaceutical, chemical, and food industries, as well as in various applications related to agriculture, biotechnology, and medicine, to name a few.

Although single-layered (core-shell) capsules were successfully fabricated by some approaches, such as compound or coaxial nozzle-based dripping/jetting, microdrop collision, and stirring/mixing-based bulk emulsification, to date the fabrication of multi-layered capsules has not been explored. The feasibility of multi-layered capsule fabrication using a coaxial dispensing mechanism and how the geometry of the resulting multi-layered capsules can be controlled by adjusting corresponding flow rates are described herein.

Fabrication of well-defined capsules with more than one shell layer still poses a significant fabrication challenge. Herein, embodiments of multi-layered capsule fabrication systems are developed and described by using a coaxial nozzle to fabricate double-layered (core-shell-shell) capsules during vibration-assisted dripping in certain aspects. During fabrication, different liquid materials can be dispensed through their corresponding channels of the coaxial nozzle to form a compound liquid flow, which can comprise a core flow, an annular flow, and a sheath flow. A high frequency vibration can be introduced to facilitate the breakup of the compound flow and the formation of double-layered capsules. Through applicable crosslinking mechanism(s) in a collection bath, capsules with a core-shell-shell structure can be fabricated.

Described herein are coaxial nozzles. Coaxial nozzles as described herein can be utilized for or configured for capsule fabrication. Coaxial nozzles as described herein can be configured for the fabrication of single- or multi-layer capsules. In embodiments, coaxial nozzles as described herein can be configured for the fabrication of double-layered capsules. In embodiments, coaxial nozzles as described herein can be configured for the fabrication of double-layered capsules having a core-shell-shell structure.

Coaxial nozzles as described herein can comprise a core flow channel, a sheath flow channel, and an annular flow channel. Channels of coaxial nozzles can reside within discreet physical structures or can be defined as the space between two or more physical structures. Channels as described herein can comprise one or more inlets configured to receive fluid. Coaxial nozzles as described herein can further comprise one or more outlet nozzles configured to output material (fluid, capsule, etc) from the coaxial nozzle. Such nozzles can be arranged as arrays for improved productivity.

In certain aspects, an annular channel can have dimensions D, $L_1$, $L_2$, and H, which are described in greater detail below and demonstrated in the figures. D can be about 7.5 mm to about 8.5 mm, $L_1$ can be about 2.0 mm to about 4.0 mm, $L_2$ can be about 12.5 to about 13.0 mm, and $L_3$ can be about 2.0 mm to about 2.5 mm. Considering the size of required multi-layered capsules, such dimensions can be adjusted from the millimeter to micrometer scale.

In certain aspects, the sheath channel can have dimensions L, $D_1$, $D_2$, and H, which are described in greater detail below and demonstrated in the figures. L can be about 1.5 mm to about 2.0 mm, $D_1$ can be about 14.0 mm to about 16.0 mm, $D_2$ can be about 11.0 mm to about 13.0 mm, and H can be about 8.0 mm to about 8.6 mm. Considering the size of required multi-layered capsules, such dimensions can be adjusted from the millimeter to micrometer scale.

In an embodiment, a coaxial nozzle can comprise three components: an inner set, a middle set, and an outer set. These components can be constructed of metal or metal alloys (such as stainless steel, titanium, aluminum, and the like), or polymers (such as polycarbonate (PC), Nylon, acrylonitrile butadiene styrene (ABS), and the like) and/or glass if special corrosive liquid materials are utilized.

An inner set can be configured to provide a core channel, and can be configured to fit with the middle set to form an annular channel.

A middle set can be in the center of a coaxial nozzle and can provide support to hold the inner set and be configured to form the annular channel as well as fit with the outer set to form the sheath channel.

An outer set can enable the formation of a sheath channel of the coaxial nozzle in addition to providing a fixture or fixture for support of the entire nozzle assembly.

The inner, middle, and outer sets can have orifices. The inner, middle, and outer sets can have orifices configured to output fluid components or materials. In certain embodiments, the through-hole in the inner set can have an inner diameter of about 0.5 mm, length of about 3.0 mm for its outer section, and outer diameter of about 1.5 mm. The outlet of the middle set can have an inner diameter of about 2.5 mm and outer diameter of about 3.5 mm. The outlet of the outer set can have an inner dimeter of about 4.5 mm. The core channel can be designed as a straight through hole in the inner set with a diameter of about 0.5 mm based on the typical core size of capsules and the machining capability.

Figure 17:
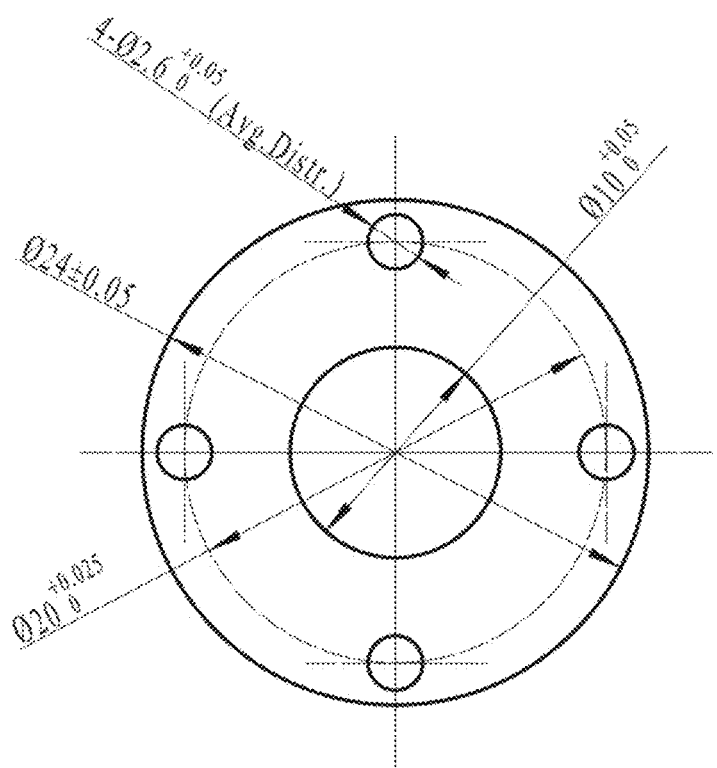
FIG. 17 is a top view of an embodiment of collar A for a coaxial nozzle as described herein.
Figure 18:
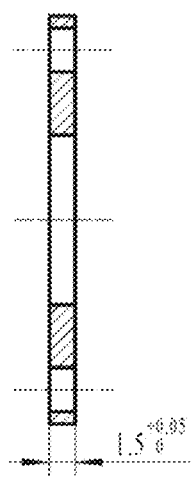
FIG. 18 is a side view of the collar of FIG. 17.
Figure 19:
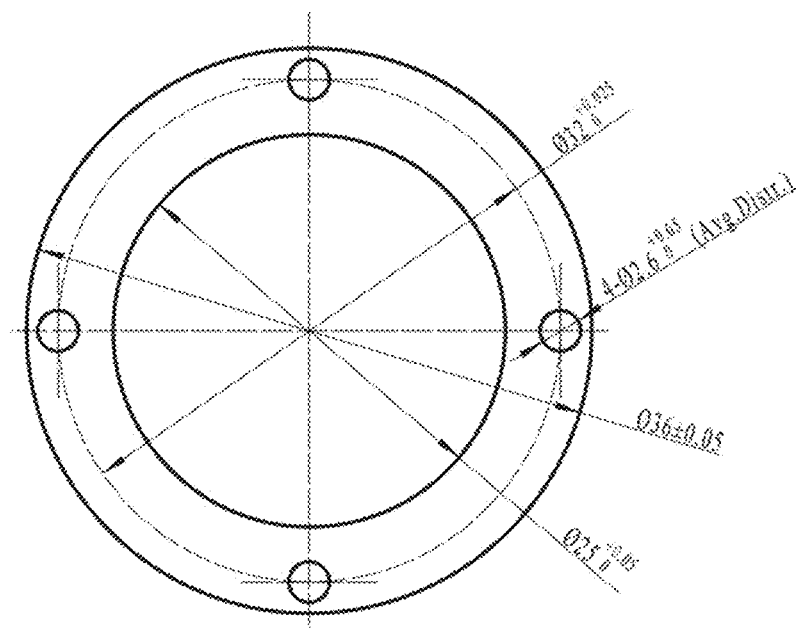
FIG. 19 is a top view of an embodiment of collar B for a coaxial nozzle as described herein.
Figure 20:
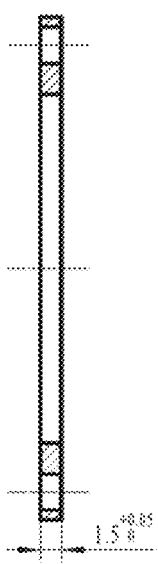
FIG. 20 is a side view of the collar of FIG. 19.
Figure 21:
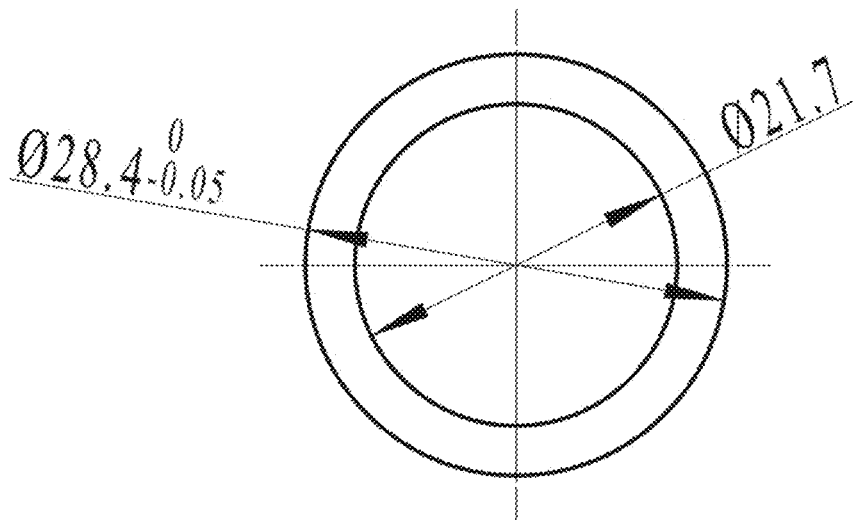
FIG. 21 is an embodiment of a gasket for a coaxial nozzle according to the present disclosure.
Figure 22:
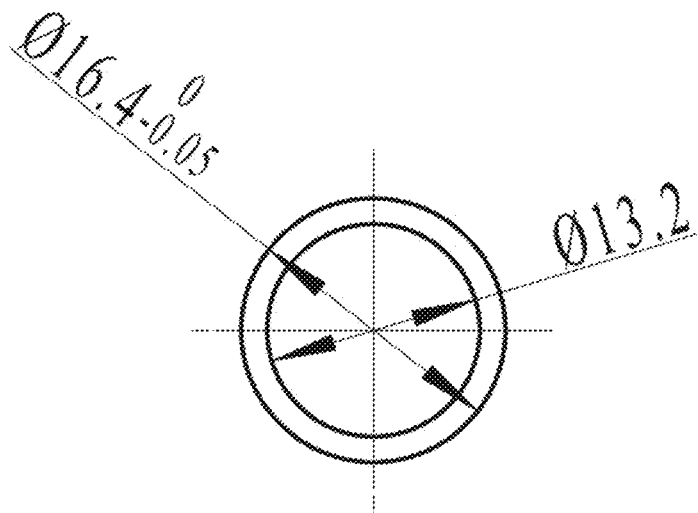
FIG. 22 is an embodiment of a second gasket for a coaxial nozzle according to the present disclosure.

Coaxial nozzles as described herein can further comprise other components such as collars, screws, and gaskets for proper operation. Screws can be configured to adjust the size or spacing of various components in order to tune operation of the nozzles. Gaskets can be copper gaskets in certain embodiments, top views of which are shown in FIGS. 21 and 22. Collar covers (embodiments of which such as those top views shown in FIGS. 17 and 19 and side view shown in FIGS. 18 and 20) can be configured to seal the space between different sets.

Figures 9, 10:
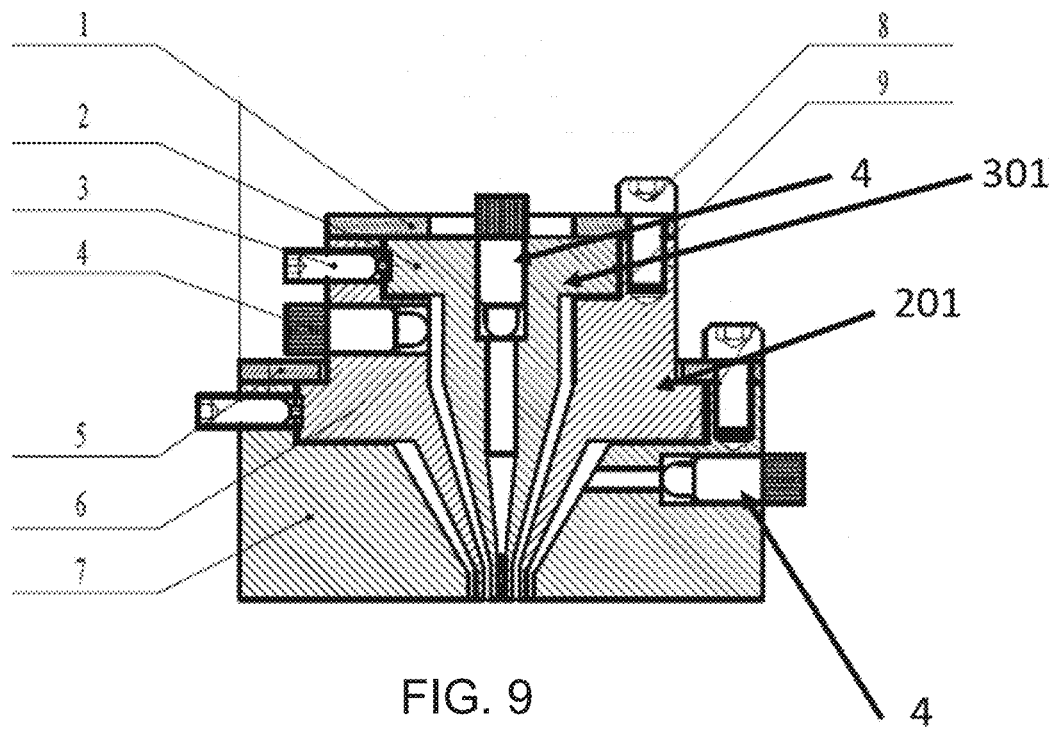
FIG. 9 is an engineering schematic of a coaxial nozzle as described herein.
FIG. 10 defines annotated portions of FIG. 9.
Figure 11:
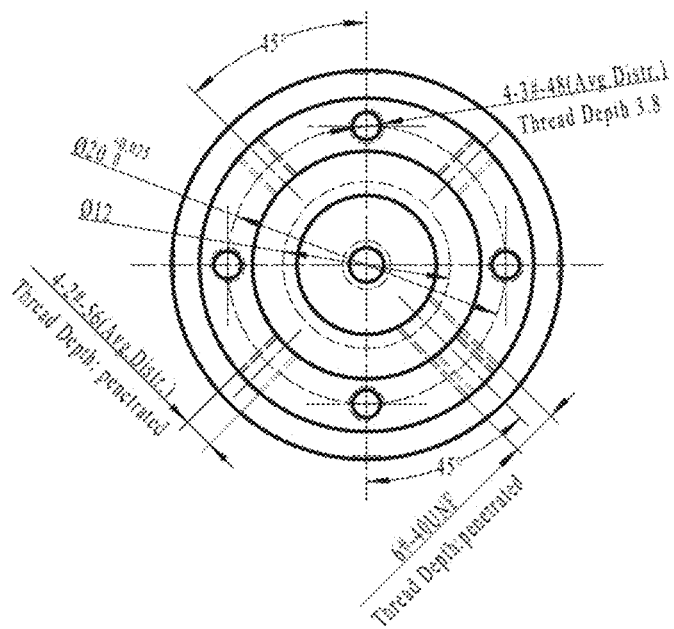
FIG. 11 is a top view of an embodiment of a middle set of a coaxial nozzle as described herein.
Figure 12:
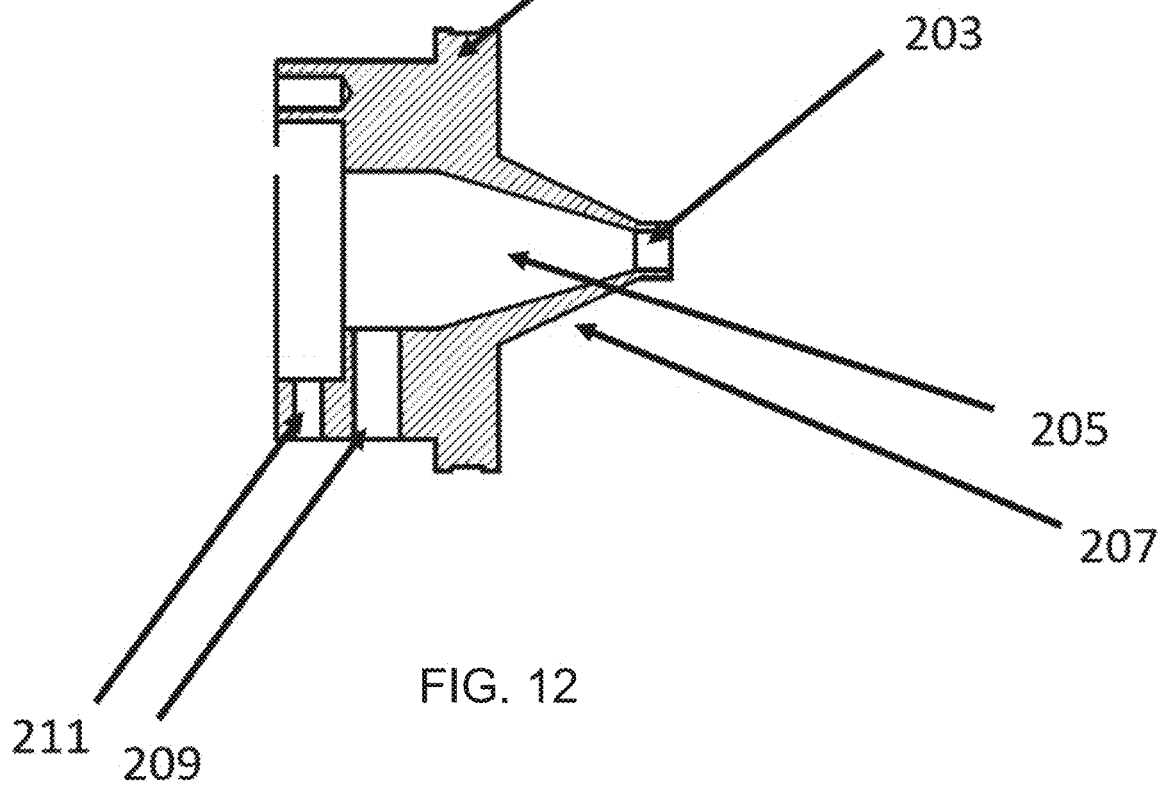
FIG. 12 is a side view of the middle set of FIG. 11.

A cross-sectional side view of an embodiment of a coaxial nozzle as described herein is shown in FIG. 9. As depicted in the side view of FIG. 9, a coaxial nozzle can be a series of nested annular structures comprising: an outer set 7 (also referred to as a die in FIG. 10) configured to a receive a middle set 6 (also referred to as a medium in FIG. 10) through a frustoconical opening, the middle set 6 in turn configured to receive an inner set 2 (also referred to as a mandrel in FIG. 10) through a frustoconical opening. The middle set 6 (top view shown in FIG. 11, additional cross-sectional view shown in FIG. 12) can have an upper lip 201 that is wider than an outlet 203, and which can rest on an upper surface of the outer set 7, or on a gasket 10 (FIG. 21 or FIG. 22) which can sit in between the upper surface of the outer set 7 and lower surface of the lip 201 of the middle set 6. The middle set 6 can have an inlet 209 for receiving a solution and/or solution supply device 4. The middle set 6 can also have a channel 211 for receiving a screw, or other adjustment device, which can aid in the positioning of the middle set 6 and inner set 2 in relation to each other. The middle set 6 can have a frustoconical opening 16 which can receive the inner set 2, the inner surface of the frustoconical opening 205 also forming a bottom surface of and partially defining the annular channel. The middle set 6 can also have an outer frustoconical surface 207 which forms the top surface of and partially defines the sheath channel.

Figure 13:
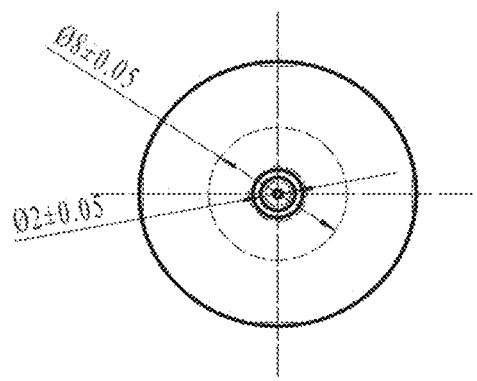
FIG. 13 is a top view of an embodiment of an inner set of a coaxial nozzle as described herein.
Figure 14:
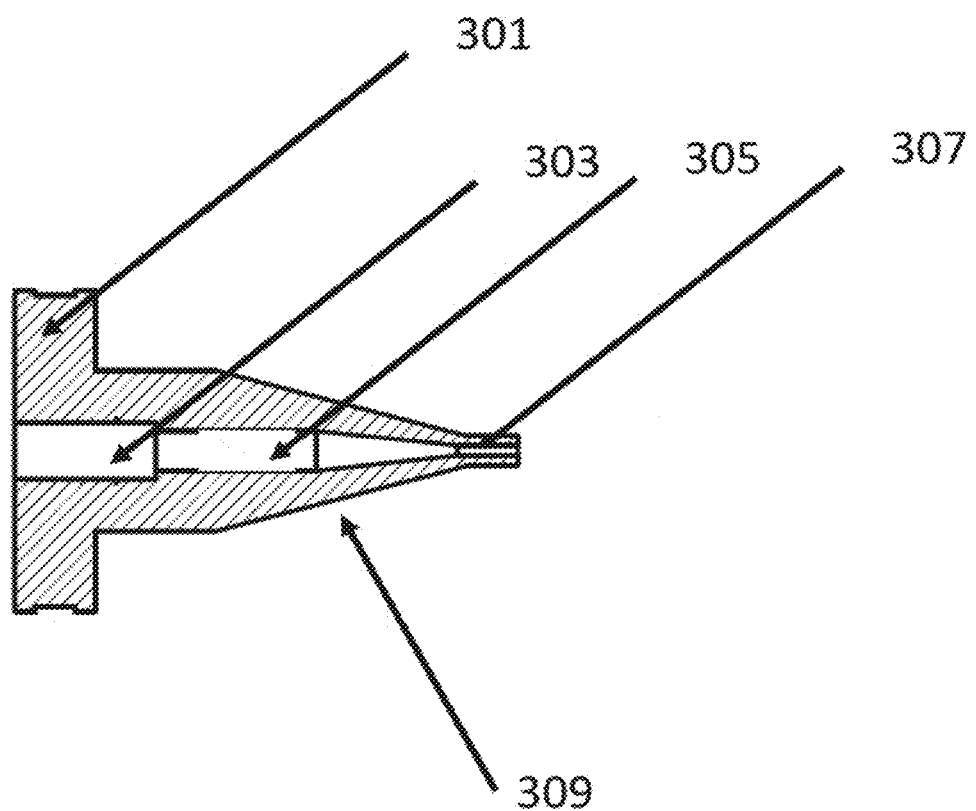
FIG. 14 is a side view of the inner set of FIG. 13.

The inner set 2 (top view shown in FIG. 13, additional cross-sectional view shown in FIG. 14) can have an upper lip 301 that is wider than an outlet 307, and which can rest on an upper surface of the middle set 6, or on a gasket 9 (FIG. 21 or FIG. 22) which can sit in between the upper surface of the middle set 6 and upper surface of the middle set 6. The inner set 2 can have an inlet 303 for receiving a solution or solution supply device 4. The inner set 2 can also have a channel 305 which functions as the core channel of the coaxial nozzle through which solution passes from the solution supply device 4 (i.e. the inlet) to the outlet 307 of the inner set 2. The inner set 2 can have a frustoconical outer surface 309 which can form a top surface of and partially define the annular channel.

Figure 15:
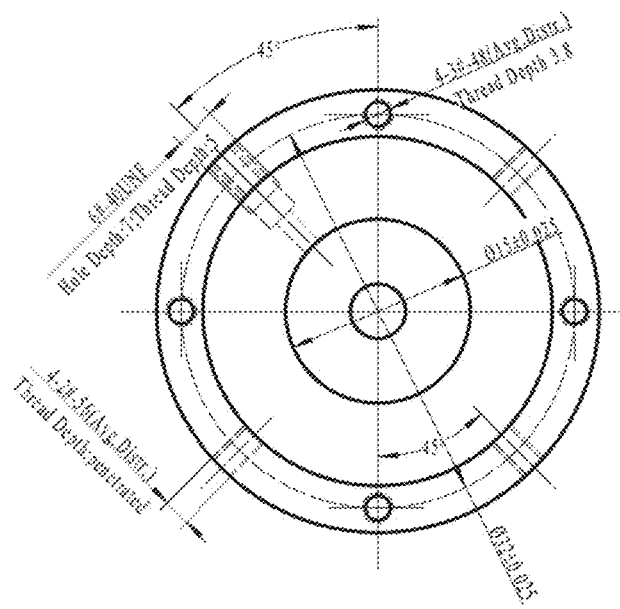
FIG. 15 is a top view of an embodiment of an outer set of a coaxial nozzle as described herein.
Figure 16:
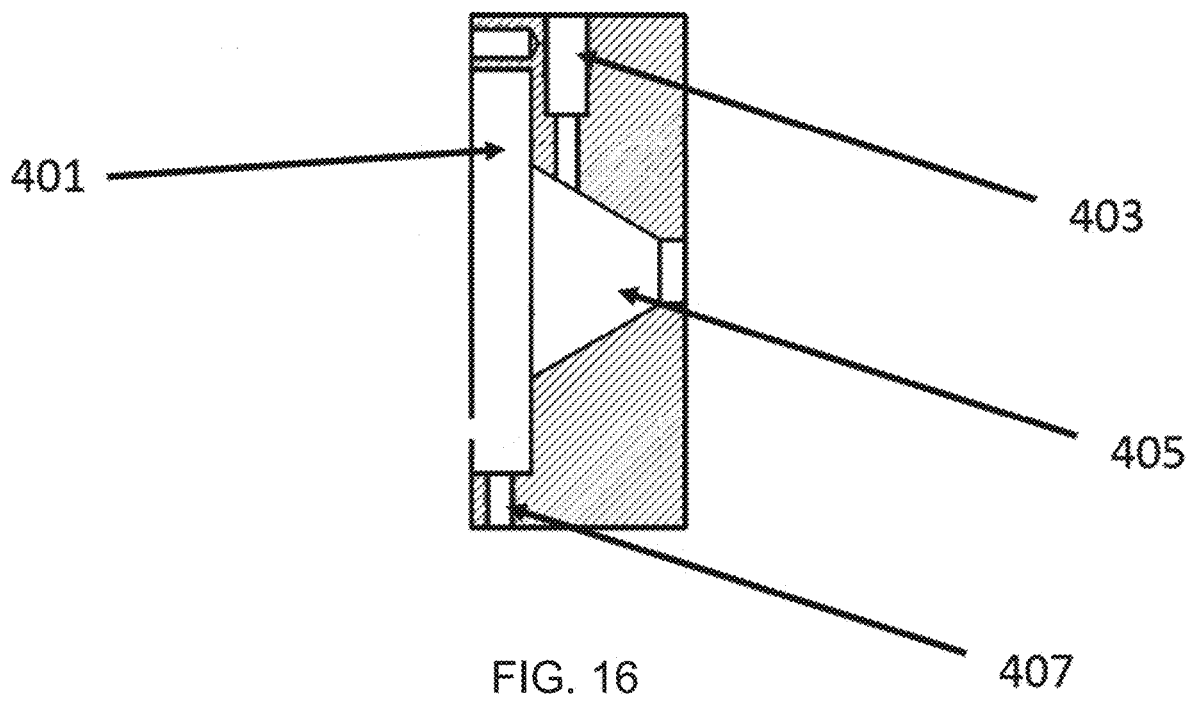
FIG. 16 is a side view of the outer set of FIG. 15.

The outer set 7 (top view shown in FIG. 15, additional cross-sectional view shown in FIG. 16) can have an upper surface 401 that receives the lip 201 of the middle set 6 or a gasket 10 (FIG. 21 or FIG. 22) which can sit in between the upper surface 401 of the outer set 7 and lower surface of the lip 201 of the middle set 6. The outer set 7 can have an inlet 403 for receiving a solution or a solution supply device 4. The outer set 7 can also have a channel 407 for receiving a screw, or other adjustment device, which can aid in the positioning of the middle set 6 and outer set 7 in relation to each other. The outer set 7 can have a frustoconical opening 405 which can receive the middle set 6, the surface of the frustoconical opening 405 also forming a bottom surface of and partially defining the sheath channel.

Although examples of dimensions of embodiments of components, shown in FIGS. 11-22, which form an embodiment of a coaxial nozzle, as shown in FIG. 9, are depicted in FIGS. 9 and 11-22, these dimensions are not intended to be limiting. One of skill in the art would understand how to scale up or scale down the coaxial nozzle or components thereof accordingly.

Described herein are capsule fabrication systems. Capsule fabrication systems as described herein can comprise one or more coaxial nozzles, such as a coaxial nozzle as described above. Capsule fabrication systems as described herein can comprise a coaxial nozzle and can be configured for the fabrication of single- or multi-layer capsules. In embodiments, capsule fabrication systems as described herein can comprise a coaxial nozzle and can be configured for the fabrication of double-layered capsules. In embodiments, capsule fabrication systems as described herein can comprise a coaxial nozzle and can be configured for the fabrication of double-layered capsules having a core-shell-shell structure.

Capsule fabrication systems as described herein can comprise a coaxial nozzle as described above, a vibrator, a collection bath, and a solution delivery system. For specific multi-layered capsule fabrication, capsule fabrication systems as described herein can comprise auxiliary systems such as temperature control and UV irradiation systems.

A vibrator can further comprise a controller which can contain a waveform generator allowing a user to alter the frequency or amplitude of the vibrations delivered to the system. Vibrator controllers as described herein can be a part of the vibrator, or can be a controller and/or a computing device existing as a separate stand-alone device in electrical communication with the vibrator. A vibrator can be attached to or in physical communication with an outer set. In embodiments, the vibrator can operate at a frequency of 100 Hz and an amplitude of 10 V.

A collection bath can be comprised of a fluid, such as calcium chloride ($CaCl_2$)). Collection baths as described herein can reside within containers configured to hold fluid. The collection bath can contain a crosslinking agent (such as $Ca^{2+}$, enzymes, and the like per the type of liquid build materials) to stabilize formed capsules.

Solution delivery systems as described herein can comprise one or more syringes or syringe-based pumps to deliver fluid to one or more channels. As described herein, each channel can have its own syringe or syringe-based pump. Solution delivery systems can be manual delivery or can be automated, in which case they can further comprise a controller or computing device to vary flow parameters of fluid delivery to the channel(s).

Described herein are methods for capsule fabrication. Methods of capsule fabrication as described herein can comprise a coaxial nozzle as described herein. Methods of capsule fabrication as described herein can comprise a capsule fabrication system comprising a coaxial nozzle. Methods as described herein can fabricate multi-layered capsules. Methods as described herein can fabricate single-layered capsules. Methods as described herein can fabricate double-layered capsules. In embodiments, methods as described herein can comprise a capsule fabrication system comprising a coaxial nozzle and can fabricate double-layered capsules. In embodiments, methods as described herein can comprise a capsule fabrication system comprising a coaxial nozzle and can fabricate multi-layered capsules.

Methods as described herein can comprise capsule initiation, capsule development, and capsule breakup. During capsule initiation, different liquid materials (such as liquid or fluid solutions containing alginate and $CaCl_2$) solutions) can be dispensed through their corresponding channels of the coaxial nozzle. Certain liquid materials are described in the examples below.

Different liquid materials can be liquid or fluid solutions, which can undergo a phase change process after forming capsules in order to retain their shape. In addition to liquid or fluid solutions containing alginate and/or liquid or fluid solutions containing $CaCl_2$), liquid materials, usually as solvent-based solutions, suspensions and/or composites, include poly(D, L-lactide-co-glycolide) (PLG), poly(1,6-bis-p-carboxyphenoxyhexane) (PCPH), alginate-collagen composites, and the like.

During capsule development, the liquid materials come together at the outlet of the coaxial nozzle to form a compound liquid flow, which can comprise a core flow, an annular flow, and a sheath flow. A high frequency vibration can then be introduced to facilitate the breakup of the compound flow and the formation of double-layered capsules herein. After crosslinking in a collection bath comprising a crosslinking agent, capsules with a core-shell-shell structure can be fabricated.

In methods as described herein, capsules can be formed at the outlet of the coaxial nozzle by dispensing various solution flows through corresponding channels, and the capsule formation process can vary based on parameters such as the velocity or flow rate of each solution and their material rheological and physical properties. The solution delivery and vibration system can comprise three syringe pumps to deliver solutions to corresponding channels and an ultrasonic vibrator to vibrate the coaxial nozzle at a given frequency and amplitude to facilitate the breakup of fluid flows and form multi-layered capsules more effectively. The collection bath herein can also contain a crosslinking agent ($Ca^{2+}$) to stabilize formed capsules.

While embodiments of the present disclosure are described in connection with the Examples and the corresponding text and figures, there is no intent to limit the invention to the embodiments in these descriptions. On the contrary, the intent is to cover all alternatives, modifications, and equivalents included within the spirit and scope of embodiments of the present disclosure.

Example 1

Multi-layered encapsulation has been of great interest for various pharmaceutical, chemical and food industries. Fabrication of well-defined capsules with more than one shell layer still poses a significant fabrication challenge. Described herein is investigation into the feasibility of using a coaxial nozzle to fabricate double-layered (core-shell-shell) capsules during vibration-assisted dripping. A three-layered coaxial nozzle is described herein. The nozzle has been designed, manufactured, and tested for double-layered capsule fabrication when using sodium alginate solutions as the model liquid material for inner and outer shell layers and calcium chloride solution as the core fluid. To facilitate the droplet formation process, a vibrator has been integrated into the fabrication system to provide necessary perturbation for effective breakup of the fluid flow. It is demonstrated that double-layered alginate capsules can be successfully fabricated using a three-layered coaxial nozzle fabrication system shown and described herein. During fabrication, increasing the core flow rate can lead to an increase in capsule and core diameters while the inner and outer shell layer thicknesses decrease. Increasing annular flow rate can result in an increase in capsule diameter and inner shell layer thickness while the outer shell layer thickness decreases. An increase in the sheath flow rate can lead to an increase in capsule diameter and outer shell layer thickness but may have no significant effect on the core diameter and inner shell layer thickness.

1. Introduction

Encapsulation, a process involving the complete envelopment of preselected core material with a well-defined porous or impermeable membrane, has been of great importance in recent years and widely used in many fields including pharmaceutical, chemical, and food industries, as well as in various applications related to agriculture, biotechnology, and medicine, to name a few. An important purpose of encapsulation is to immobilize, protect, and control the release of entrapped materials such as flavor, living cells, and pharmaceutical compounds.

For the fabrication of multi-layered capsules, various technologies have been studied, including compound or coaxial nozzle-based dripping/jetting, microdrop collision, and stirring/mixing-based bulk emulsification. During compound or coaxial nozzle-based fabrication, coaxial nozzles can be used to produce the core droplet surrounded by a shell. When the flow rates of core and shell solutions increase, the droplet formation mechanism may change from dripping to jetting. A liquid core jet can be surrounded by an annular jet, which may be further surrounded by a carrier stream. For some applications, additional stimuli may be applied to facilitate the droplet formation process such as an electric field (for example, as described in Lopez-Herrera, J. M., Barrero, A., Lopez, A., Loscertales, I. G., and Marquez, M., 2003, "Coaxial Jets Generated from Electrified Taylor Cones," Journal of Aerosol Science, 34(5), pp. 535-552.; Loscertales, I. G., Barrero, A., Guerrero, I., Cortijo, R., Marquez, M., and Ganan-Calvo, A. M., 2002, "Micro/Nano Encapsulation via Electrified Coaxial Liquid Jets," Science, 295(5560), pp. 1695-1698; Yao, R., Zhang, R., Luan, J., and Lin, F., 2012, "Alginate and Alginate/Gelatin Microspheres for Human Adipose-Derived Stem Cell Encapsulation and Differentiation," Biofabrication, 4(2), pp. 025007; and Yao, R., Zhang, R., Lin, F., and Luan, J., 2012, "Injectable Cell/Hydrogel Microspheres Induce the Formation of Fat Lobule-Like Microtissues and Vascularized Adipose Tissue Regeneration," Biofabrication, 4(4), pp. 045003, the entirety of all of which are incorporated by reference herein) or vibration (for example as described in Berkland, C., Pollauf, E., Varde, N., Pack, D. W., and Kim, K. K., 2007, "Monodisperse Liquid-Filled Biodegradable Capsules," Pharmaceutical Research, 24(5), pp. 1007-1013.; Yao, R., Zhang, R., Lin, F., and Luan, J., 2012, "Injectable Cell/Hydrogel Microspheres Induce the Formation of Fat Lobule-Like Microtissues and Vascularized Adipose Tissue Regeneration," Biofabrication, 4(4), pp. 045003; and Heinzen, C., Marison, I., Berger, A., and von Stockar, U., 2002, "Use of Vibration Technology for Jet Break-Up for Encapsulation of Cells, Microbes and Liquids in Monodisperse Capsules," Landbauforschung Völkenrode, SH241, pp. 19-25., the entirety of all of which are incorporated by reference fully herein). During microdrop collision, two inkjet nozzles can be utilized to make droplets from different solutions such as aqueous and polymer solutions. After the collision of two inkjetted droplets, a polymer film can be generated at the interface between two solutions due to the solvent exchange mechanism, and a compound droplet can be fabricated with the polymer solution as the shell layer. During stirring/mixing-based bulk emulsification, two emulsification steps can be adopted: a core material can be stirred into a shell polymer solution, and the formed emulsion can be further stirred into an emulsifier-based solution to form double-layered emulsions. The process can be improved by combining the co-nozzle extrusion with emulsification. By using a microcapillary device, the coaxial flow can be formed at the exit of a tapered tube, and the outermost fluid can be pumped through the outer coaxial region from the opposite direction; as the compound flow passes through the exit orifice, it ruptures into core-shell capsules. While this approach simplifies the two emulsification step-based conventional fabrication process, the outermost fluid can be used to emulsify the coaxial flow into core-shell capsules instead of being a layer of the capsules. In addition, it is difficult to fabricate a double-layered coaxial glass microcapillary device as well as to control the formation of a three-layered compound flow in an emulsification flow.

Thus, it may not be practical to extend this approach to fabricate capsules with a well-defined core-shell-shell structure.

Described herein is an embodiment of a coaxial nozzle to fabricate multi-layered capsules, for example double-layered (core-shell-shell) capsules during vibration-assisted dripping. Of the fabrication technologies described above, compound or coaxial nozzle-based dripping/jetting can be favored due to its simple implementation. As expected, the multi-layered capsule fabrication process can produce monodisperse capsules with one core material enclosed by more than one surrounding shell material. Although single-layered (core-shell) capsules were successfully fabricated by the aforementioned fabrication approaches, to date the fabrication of multi-layered capsules has not been explored.

The disclosure herein describes the first investigation of the feasibility of multi-layered capsule fabrication using embodiments of the coaxial dispensing mechanism and how the geometry of the resulting multi-layered capsules can be controlled by adjusting corresponding flow rates. Sodium alginate (NaAlg) has been selected in this disclosure as the model hydrogel material to fabricate double-layered capsules, and calcium chloride can be used as the crosslinking agent to facilitate the formation of alginate capsules. To facilitate the droplet formation process, ultrasonic vibration can be applied to the coaxial nozzle during dripping. The embodiment of a coaxial nozzle-based multi-layered capsule fabrication system has been validated during the fabrication of multi-layered capsules, such as double-layered alginate capsules, providing a versatile approach for effective capsule fabrication. While alginate and calcium chloride solutions are utilized as examples throughout the present disclosure, the devices and approaches as described here can also be applicable to other capsule fabrication techniques, such as capsule fabrication from suspensions for example.

2. Coaxial Nozzle-Based Fabrication Approach

A schematic of an embodiment of a multi-layered capsule fabrication system is illustrated in FIG. 1A. During fabrication, different liquid materials can be dispensed through their corresponding channels of the coaxial nozzle to form a compound liquid flow, which comprises a core flow, an annular flow, and a sheath flow. A high frequency vibration can be introduced to facilitate the breakup of the compound flow and the formation of double-layered alginate capsules herein. After crosslinking in a collection bath, capsules with a core-shell-shell structure can be fabricated. As shown in FIG. 1A, the multi-layered capsule fabrication system can comprise three components: a multi-layered coaxial nozzle, a solution delivery and vibration system, and a collection bath. An important aspect of the multi-layered capsule fabrication system is the three-layered coaxial nozzle (inset of FIG. 1A), which can enable capsule fabrication and can influence the geometry of fabricated capsules. The nozzle can comprise a core flow channel to form the core layer, an annular flow channel to form the inner shell layer, and a sheath flow channel to form the outer shell layer of double-layered capsules. Capsules can be formed at the outlet of the coaxial nozzle by dispensing various solution flows through corresponding channels, and the capsule formation process can vary based on parameters such as the velocity or flow rate of each solution and their material rheological and physical properties. The solution delivery and vibration system can comprise three syringe pumps to deliver solutions to corresponding channels and an ultrasonic vibrator to vibrate the coaxial nozzle at a given frequency and amplitude to facilitate the breakup of fluid flows and form multi-layered capsules more effectively. The collection bath herein can also contain a crosslinking agent ($Ca^{2+}$) to stabilize formed capsules.

An embodiment of a multi-layered capsule fabrication system and schematic is illustrated in FIG. 1A. FIG. 1B illustrates an embodiment of the fabrication process of a double-layered capsule with images showing three representative sequential stages during fabrication: capsule initiation, development, and breakup. Such a system can be used to fabricate double-layered capsules by delivering corresponding solutions through the core flow, annular flow, and sheath flow channels, individually in a sequence or simultaneously. While using the core and annular flow channels only (or using the sheath flow channel only to provide a carrier stream for jet pinch-off control), it can also be utilized to fabricate single-layered (core-shell) capsules. Due to simple implementation, the multi-layered capsule fabrication system can be applicable to the fabrication of various single- and double-layered capsules from diverse liquid materials in conjunction with suitable crosslinking mechanisms.

3. Material Selection and Nozzle Design 3.1 Material Selection

Throughout the present disclosure, sodium alginate, a natural polysaccharide, was selected as a model material to fabricate the shell layers of double-layered capsules due to its versatile functionality, mild crosslinking conditions, low cost, biocompatibility, low toxicity, and environmentally friendly nature, as well as its wide applications for encapsulation. As designed, alginate solutions can be dispensed through the annular and sheath flow channels to form two shell layers each with a different dye for layer distinction. Aqueous calcium chloride ($CaCl_2$) was selected as the core flow as well as collection bath material, acting as the crosslinking agent for alginate. Sodium alginate comprises a family of unbranched binary copolymers of 1,4 linked β-D-mannuronic acid (M units) and α-L-guluronic acid (G units). When it interacts with divalent ions such as $Ca^{2+}$ or trivalent ions such as $Al^{3+}$, it can undergo an ionic gelation process, which can occur as such cations form interchain ionic bonds between G blocks, giving rise to a stable three-dimensional network of calcium alginate.

3.1.1 Gelation Process Modeling

The $CaCl_2$ concentration of the core flow can affect the gelation rate of the annular alginate flow when traveling in air. If the $CaCl_2$ concentration is too high, the sodium alginate solution can gel immediately once dispensed out of the nozzle, resulting in a gelled filament before forming a droplet. If the $CaCl_2$ concentration is too low, the gelation rate of the inner surface of the inner shell layer can be slow, which can result in undesirable diffusion between the sodium alginate and $CaCl_2$ solutions. As a result, the inner surface of the inner shell layer may not be well-defined. Thus, it is important to select a suitable $CaCl_2$ concentration to fabricate well-defined multi-layered alginate capsules.

Since the $CaCl_2$ concentration of the core flow can be of interest, FIG. 2A illustrates the interaction between the $CaCl_2$ core flow and the alginate annular flow. When the alginate solution is dispensed into the ambient environment, it can start interacting with the $CaCl_2$ core flow.

The reaction front during alginate gelation is defined as the region where the most chemical crosslinking takes place and spatially separates the newly gelled region from the fluid ungelled alginate region as shown in FIG. 2A. Based on the traveling-wave hypothesis and diffusive flux of calcium cations through a gelled structure (as described in Xiong, R., Zhang, Z., Chai, W., Huang, Y., and Chrisey, D. B., 2015, "Freeform Drop-on-Demand Laser Printing of 3D Alginate and Cellular Constructs," Biofabrication, 7(4), pp. 045011-1-13, which is fully incorporated by reference herein), the reaction front position G(t), the distance from the inner boundary of a single-layered capsule to the edge of the reaction front, can be obtained as a function of time t as follows (as described in Braschler, T., Valero, A., Colella, L., Pataky, K., Brugger, J., and Renaud, P., 2011, "Link between Alginate Reaction front Propagation and General Reaction Diffusion Theory," Analytical Chemistry, 83(6), pp. 2234-2242, which is fully incorporated by reference herein):

$$1 + \theta = \left(1 + \frac{L_d}{D_c}\frac{dG(t)}{dt}\right)\exp\left(\frac{1}{D_c}G(t)\frac{dG(t)}{dt}\right) \quad (1)$$

$$\theta = \frac{c_0}{N_c a_0} \quad (2)$$

where θ is defined as a shorthand notation of the calcium cation bulk concentration $c_0$ with respect to the concentration of available binding sites $N_c a_0$, $N_c$ is the stoichiometric calcium cation-binding capacity per alginate residue and can be estimated based on the half-eggbox model as $N_c = \frac{3}{4}\sigma$ (as described in Morris, E. R., Rees, D. A., Thom, D., and Boyd. J., 1978, "Chiroptical and Stoichiometric Evidence of a Specific, Primary Dimerisation Process in Alginate Gelation," Carbohydrate Research, 66(1), pp. 145-154., which is fully incorporated by reference herein), where σ is the guluronic acid content of alginate and equals 70% in this disclosure, $a_0$ is the initial bulk concentration of alginate solution in terms of uronic acid residues and equals 0.025 mol/L in this disclosure, $L_d$ is the equivalent filter length for the reaction-diffusion model system (by assuming that all the diffusion happens along the radial direction, $L_d$ equals 0 in this disclosure), and $D_c$ is the diffusion coefficient of free calcium cations, which can be interpolated based on the diffusion coefficient measurement of calcium cations (as described in Wang, J. H., 1953, "Tracer-Diffusion in Liquids. IV. Self-Diffusion of Calcium Ion and Chloride Ion in Aqueous Calcium Chloride Solutions," Journal of the American Chemical Society, 75(7), pp. 1769-1770., which is fully incorporated herein by reference) with different bulk concentrations. By assuming a steady-state concentration gradient of calcium cations, the steady-state analytical formula of G(t) can be obtained as follows (as described in Braschler, T., Valero, A., Colella, L., Pataky, K., Brugger, J., and Renaud, P., 2011, "Link between Alginate Reaction front Propagation and General Reaction Diffusion Theory," Analytical Chemistry, 83(6), pp. 2234-2242, which is fully incorporated by reference herein):

$$G(t) = \sqrt{2D_c\theta t + L_d^2} - L_d \quad (3)$$

The gelation time can be approximated as the breakup period as described herein, which can be affected by the material properties and flow rate of the core and shell flows. By considering that the longest breakup period can be on the order of 1 s (~3 s) and the typical annular shell thickness of capsule can be on the order of 0.1 mm (~0.5 mm), the reaction front position G(t) of $CaCl_2$ core flow solution with different concentrations can be calculated. If G(t) is taken as one-tenth of the annular shell thickness, that is assumed to be 0.5 mm, the alginate gelation of the inner surface of the inner shell layer may not significantly affect the jet/flow breakup and capsule formation process. When the CaCl$_2$) concentration decreases to 0.5% (w/v), G(t) is around 0.03 mm (where $c_0=0.275\times10^{-2}$ mol/L and $D_c\sim0.71\times10^{-9}$ m$^2$/s), which is lower than 0.05 mm. As such, the CaCl$_2$) concentration of the core flow is selected as 0.5% (w/v) herein.

After an alginate capsule submerges in the CaCl$_2$) collection bath, its crosslinking mechanism is depicted in FIG. 2B. To maintain its spherical morphology, the outer surface of alginate capsules can be solidified in a timely manner. Thus, a 2.0% (w/v) CaCl$_2$) solution was used as the crosslinking and collection bath. Finally, alginate capsules can be completely crosslinked in the bath as shown in FIG. 2C.

3.1.2 Material Preparation

Sodium alginate (Sigma-Aldrich, St. Louis, Mo.) was used to fabricate the layers of multi-layered capsules: 1.0% (w/v) alginate solution for the annular flow and 2.0% (w/v) alginate solution for the sheath flow. During preparation, alginate powder was dissolved in deionized (DI) water with continuous stirring until completely dissolved. To distinguish different alginate layers of fabricated double-layered capsules, fluorescent blue 7-Amino-4-methylcoumarin (Chem-Impex, Wood Dale, Ill.) was added to the 1.0% (w/v) alginate solution at a concentration of 0.5% (w/v), and fluorescent green polyethylene microspheres (UVPMS-BG-1.00, 45-53 µm, Cospheric LLC, Santa Barbara, Calif.) were added to the 2.0% (w/v) alginate solution at a concentration of 0.5% (w/v).

Calcium chloride (CaCl$_2$); Sigma-Aldrich, St. Louis, Mo.) was used to crosslink the alginate solutions during capsule fabrication. CaCl$_2$) solution was prepared by dissolving CaCl$_2$) powder in DI water with continuous stirring until completely dissolved. Specifically, 0.5% (w/v) CaCl$_2$) solution was prepared as the core flow to crosslink the inner surface of alginate capsules while 2.0% (w/v) CaCl$_2$) solution was prepared as the crosslinking bath to crosslink fabricated alginate capsules as aforementioned.

3.1.3 Rheological Properties Measurement and Results

Rheological properties of alginate solutions with different concentrations (1.0% and 2.0% (w/v)) were measured using a rheometer (ARES LS1, TA, New Castle, Del.) with a cone-plate measuring geometry (a diameter of 50 mm, a cone-to-plate gap distance of 46 µm, and a cone angle of 2.64°). To quantitatively determine the viscosity, steady rate sweeps were conducted by varying the shear rate from 0.01 to 100 s$^{-1}$. By fitting the shear stress-rate data into the Carreau-Yasuda model, the zero-shear-rate viscosity can be obtained as shown in FIG. 7 (Table 1). The surface tension was measured using a tensiometer (DSA10-MK2, Krüss GmbH, Hamburg, Germany) based on the pendant drop method, and the results are listed in FIG. 7 (Table 1).

Figures 3A, 3B, 3C:
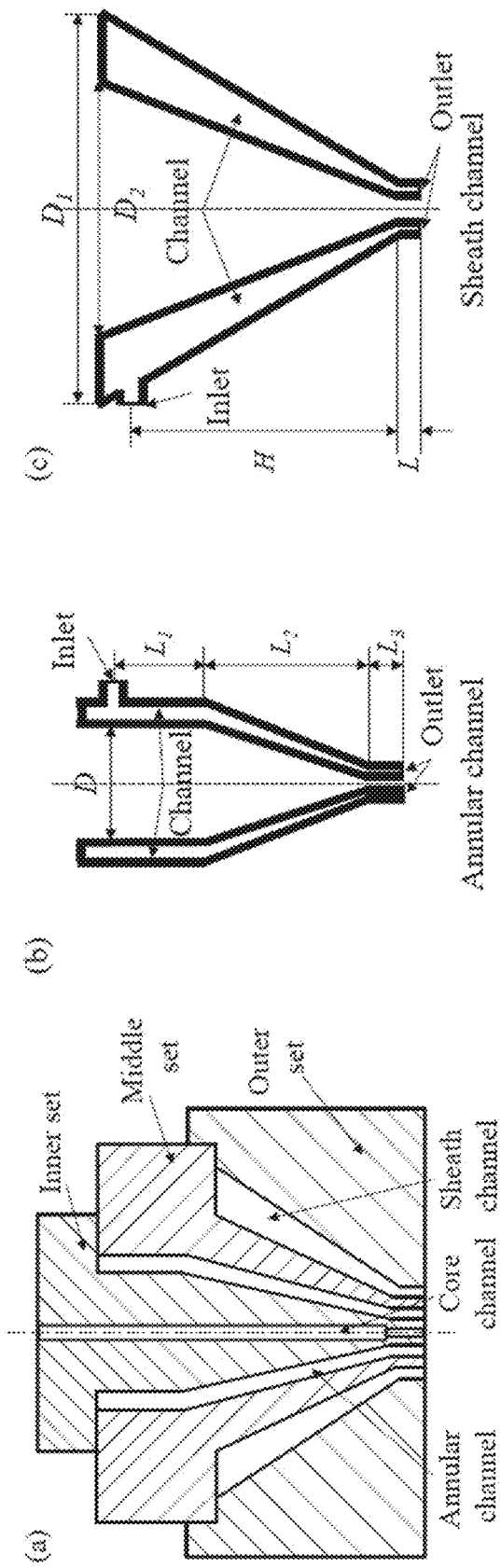
FIGS. 3A-3F depict a structure of an embodiment of a three-layered coaxial nozzle and simulation results thereof.

3.2 Three-Layered Coaxial Nozzle Design and Fabrication 3.2.1 Three-Layered Coaxial Nozzle Design Embodiments of three-layered coaxial nozzles according to the present disclosure can comprise three stainless steel components: an inner set, a middle set, and an outer set as shown in FIG. 3A. In addition to the three sets, FIG. 3A also illustrates three channels for fluid dispensing: core, annular, and sheath channels. The inner set can have two functions: to provide the core channel for the core flow, and to fit with the middle set to form the annular channel as shown in FIG. 3B. The middle set can be in the center of the coaxial nozzle and can provide support to hold the inner set to form the annular channel as well as fit with the outer set to form the sheath channel. The outer set can enable the formation of the sheath channel of the coaxial nozzle as shown in FIG. 3) in addition to being the fixture of the whole nozzle assembly. The coaxial nozzle can also be attached to the vibrator via the outer set. Due to the interest in capsule fabrication and the capacity in micromachining of the stainless steel nozzle sets, the orifice size of each set can have dimensions as follows. The through-hole in the inner set can have an inner diameter of 0.5 mm, length of 3.0 mm for its outlet section, and outer diameter of 1.5 mm; the outlet of the middle set can have an inner diameter of 2.5 mm and outer diameter of 3.5 mm; and the outlet of the outer set can have an inner diameter of 4.5 mm as shown in FIG. 3A.

The core channel can be designed as a straight through hole in the inner set with a diameter of 0.5 mm based on the typical core size of capsules and the machining capability. FIGS. 3B and C illustrate the embodiments of structures of both annular and sheath channels. As seen from these two figures, alginate solutions can be injected into the channels from their corresponding inlets, which are perpendicular to the axis of the nozzle. Thus, it is relevant to design the nozzle assembly for uniform flow fields in the channels and at the outlet of the nozzle in order to have well-defined capsules. Specifically, for the annular channel (FIG. 3B), the shaping length $L_3$, the compression angle (determined by the inner diameter D and axial length $L_2$), and the distance from the inlet to the inclined channel $L_1$ are to be determined; for the sheath channel (FIG. 3C), the shaping length L, the compression angle (determined by the inner diameter $D_2$ and distance from the inlet to the shaping section H), and the outer diameter $D_1$ are also to be determined. Considering the machining capability, the ranges of these structure dimensions can be selected as shown in FIG. 8 (Table 2).

The aforementioned structural dimensions can be determined by achieving the uniformity of the flow velocity distribution at the nozzle outlet. As described herein, the numerical simulation and analysis of velocity distribution can be performed using FLUENT 15.0 (ANSYS, Canonsburg, Pa., USA) to determine the optimal design for the three-layered coaxial nozzle. During simulation, the meshes can be automatically generated, the volume flow rate in the annular channel can be set to 800 µL/min and that in the sheath channel can be set to 1600 µL/min, and the inside walls can be set as non-slip. Based on the experimental design, the 1.0% and 2.0% (w/v) NaAlg solutions are used as the annular and sheath flows, respectively, for simulations.

Figure 3F:
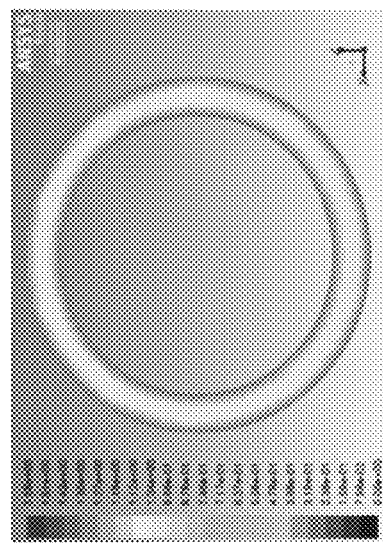
Figure 3E:
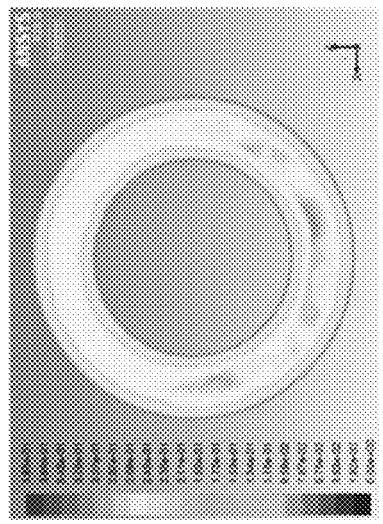
Figure 3D:
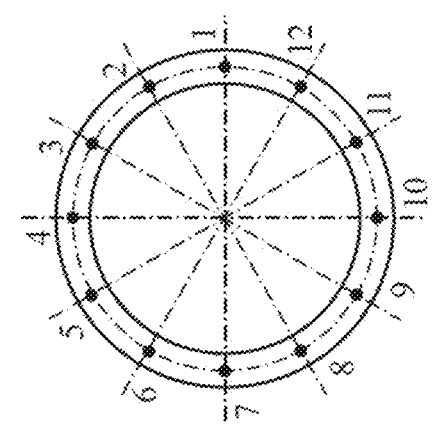
Figure 23:
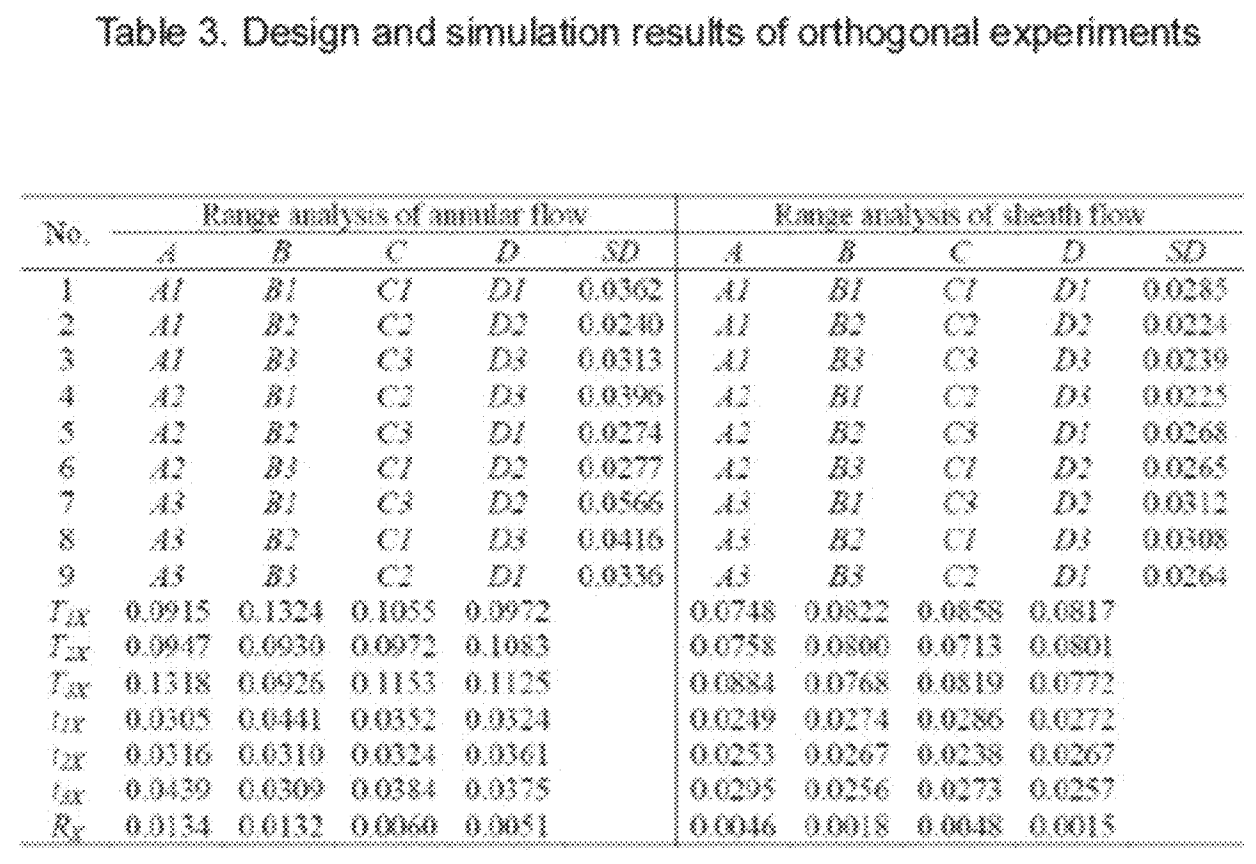

The numerical simulation of the effects of these structure dimensions on the flow velocity uniformity is performed using an orthogonal experiment ($L_9$ ($3^4$)) based on the factor and level numbers as shown in FIG. 8 (Table 2). Overall, nine different combinations of these structure dimensions can be selected accordingly as the orthogonal experimental design (FIG. 23). To evaluate the uniformity of the velocity field at the outlet of the nozzle, twelve points along the circumferential direction at the cross-sectional area of the outlet can be selected with an interval angle of 30° as shown in FIG. 3D. The velocities at these 12 points are collected and the standard deviation of the velocity $$SD = \sqrt{\frac{1}{N}\sum_{i=1}^{N}(x_i - \bar{x})^2}$$

is calculated as the criteria to assess the uniformity of the velocity at the outlet, where, SD is the standard deviation of the velocity, N is the number of the evaluated points (N=12 herein), $x_i$ is the velocity of $i^{th}$ point, and $\bar{x}$ is the average velocity. For illustration, some typical velocity distributions of the annular and sheath flows at the outlet of the nozzle are shown in FIGS. 3E and 3F. Based on the orthogonal experiment results as shown in FIG. 23, a combination of the structural dimensions can be: annular channel (D=7.50 mm, $L_1$=3.00 mm, $L_2$=12.75 mm, and $L_3$=2.25 mm) and sheath channel (L=1.50 mm, $D_1$=15.00 mm, $D_2$=12.00 mm, and H=8.28 mm) to minimize the SD values of the simulation results.

3.2.2 Three-Layered Coaxial Nozzle Manufacturing

Figures 4A, 4D, 4E:
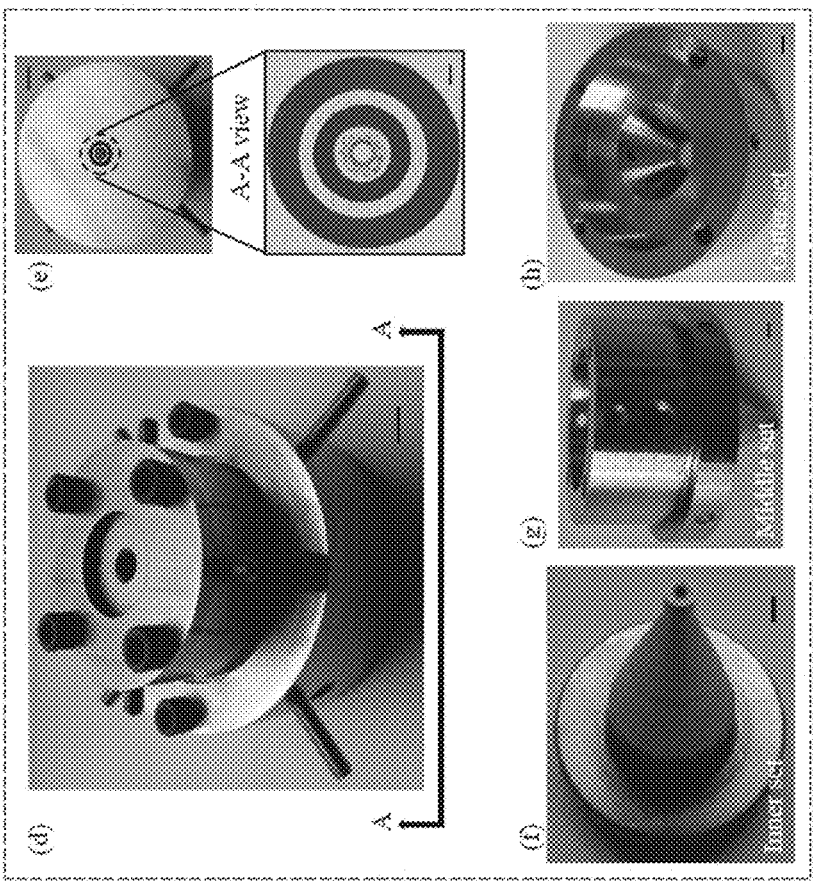
FIGS. 4A-4H illustrate an embodiment of a three-layered coaxial nozzle as described herein.
Figures 4B, 4C:
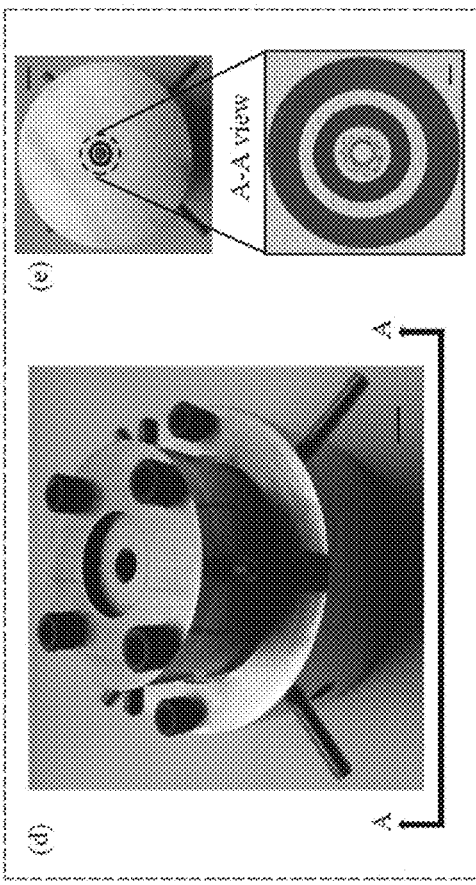
Figures 4F, 4G:
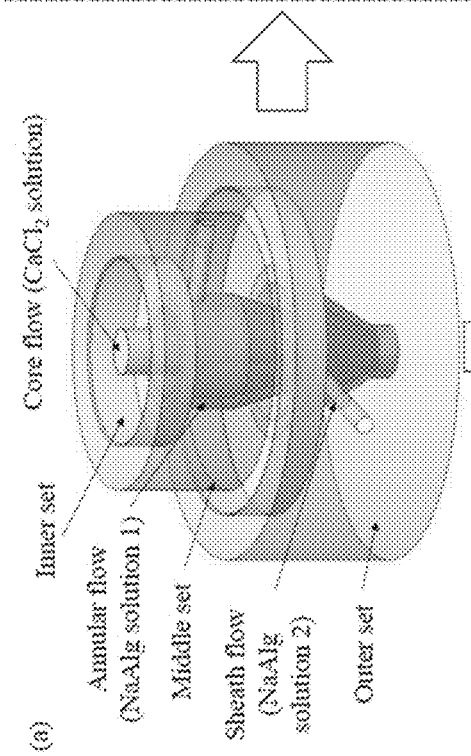
Figure 4H:
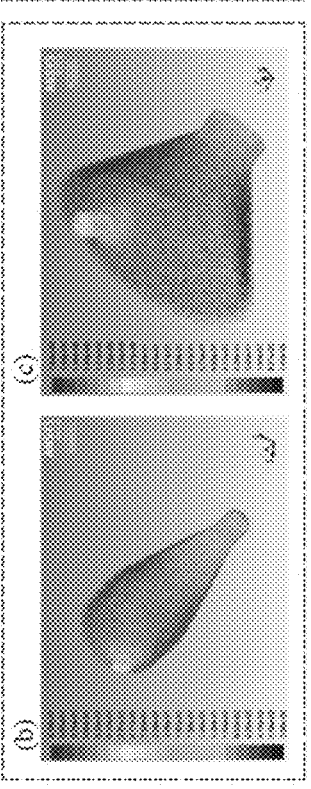

Based on the optimization of the three-layered coaxial nozzle design, a stainless steel nozzle was manufactured. The schematic of an embodiment of a three-layered coaxial nozzle structure is illustrated in FIG. 4A, and the corresponding velocity field distribution in the annular and sheath channels as simulated are shown in FIGS. 4B and 4C. When flowing in the channels, the solutions can have a uniform velocity distribution, and the velocity can increase evenly in the compression section until the solutions are dispensed out of the nozzle.

Embodiments of the fabricated inner (FIG. 4F), middle (FIG. 4G), and outer (FIG. 4H) sets are also shown in FIG. 4, and they can be assembled together and fixed by eight bolts as shown in FIG. 4D. To avoid the leakage along any interfaces, copper gaskets can be used between each two connected parts. To ensure the coaxial alignment of these three channels, four bolts can be used to adjust the position of the inner set in the middle set, and another four bolts can be used to adjust the position of the inner-middle set subassembly in the outer set as shown in FIG. 4D. After assembly, fine adjustments for optimal coaxial alignment of the channels can be performed under a microscope as shown in FIG. 4E.

3.3 Experimental Setup and Design

The core ($CaCl_2$)), annular (NaAlg in blue) and sheath (NaAlg in green) solutions were provided at different flow rates accordingly using three independent syringe pumps (Harvard Apparatus, Holliston, Mass.). The three-layered coaxial nozzle as a whole can be attached to an ultrasonic vibrator (Etrema Product, Ames, Iowa), which can be driven by an amplified waveform from a waveform generator (33522A, Agilent Technologies, Englewood, Colo.). Specifically, the waveform can be a sinusoidal wave with a frequency of 100 Hz and an amplitude of 10 V.

To investigate the effects of flow rate on the capsule geometry, different flow rates can be used to fabricate double-layered capsules. The investigated core flow rates were: 100, 200, and 300 μL/min, the annular flow rates were: 600, 800, and 1000 μL/min, and the sheath flow rates were: 1200, 1600, and 2000 μL/min. After the dissection of gelled capsules, they were imaged using a fluorescence microscope (EVOS FL, ThermoFisher Scientific, Waltham, Mass.) with the green fluorescent and blue fluorescent channels to distinguish two alginate shell layers. The boundary between the outer and inner layers was determined by finding the most significant color difference. All quantitative values of capsule dimensions were reported as mean±standard deviation with three samples per group. Statistical analysis was performed using the analysis of variance (ANOVA), and p-values of less than 0.05 were considered statistically significant.

4. Fabrication Results 4.1 Representative Double-Layered Capsules

Figure 5A:
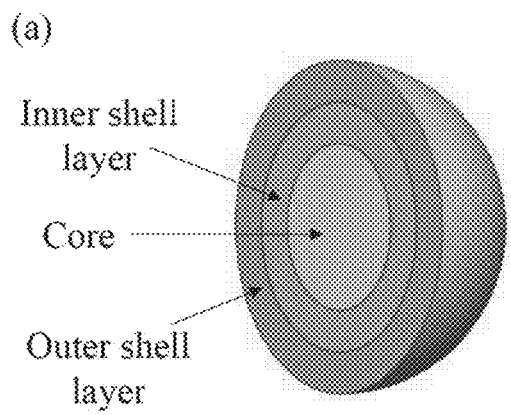
FIG. 5A is a schematic of an embodiment of a double-layered capsule.

By adjusting the flow rates of core, annular, and sheath flows, well-defined double-layered capsules can be fabricated at a frequency of about 20 capsules/minute based certain setups. FIG. 5A shows a schematic of embodiments of double-layered capsules comprising a core layer surrounded by inner and outer shell layers. After fabrication, capsules can be submerged in the $CaCl_2$) bath for 20 minutes for complete gelation, and representative gelled capsules are shown in FIG. 5B.

Figure 5B:
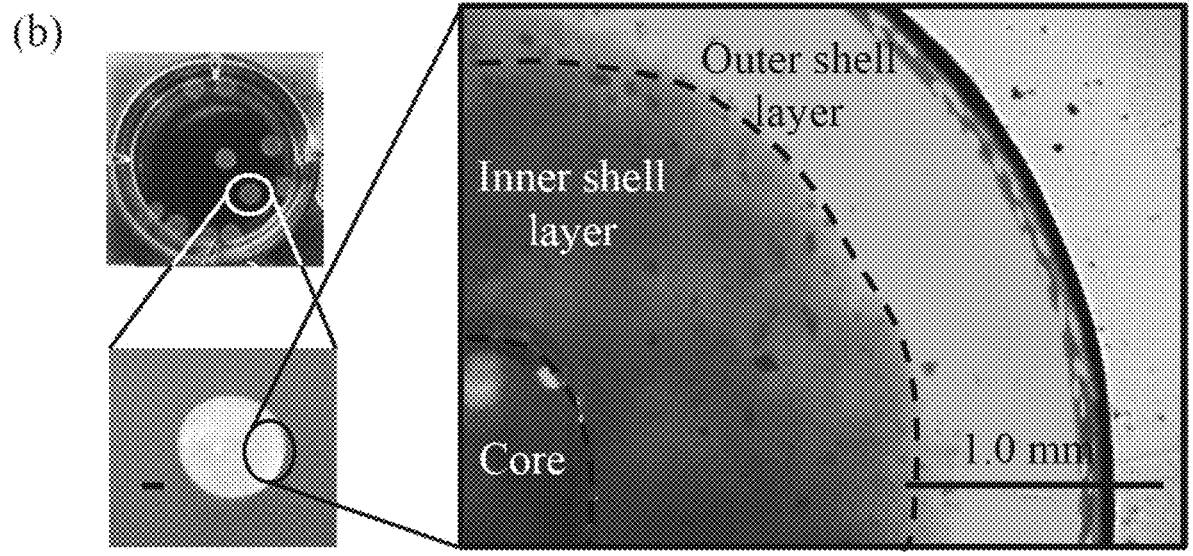
FIG. 5B are photographs showing embodiments of representative alginate capsules. Scale bars are 1.0 mm.

Furthermore, FIG. 5B inset shows a dissected capsule after complete gelation, and the florescent image of its hemisphere is captured by fluorescence microscopy. As seen from the inset, the inner and outer shell layers are clearly distinguishable with a relatively uniform thickness for each layer, proving the effectiveness of the multi-layered capsule fabrication system for the fabrication of double-layered capsules with well-defined geometry.

4.2 Effects of Core, Annular, and Sheath Flow Rates on Capsule Geometry

Figure 6A:
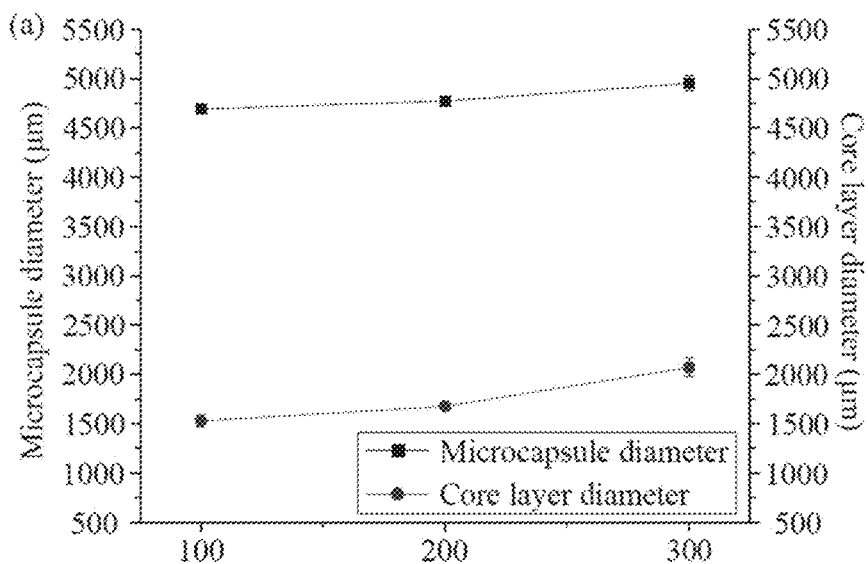
FIGS. 6A-6F comprise graphs showing the effects of flow rates on the dimensions of double-layered capsules produced by embodiments of nozzles and systems as described herein.
Figure 6B:
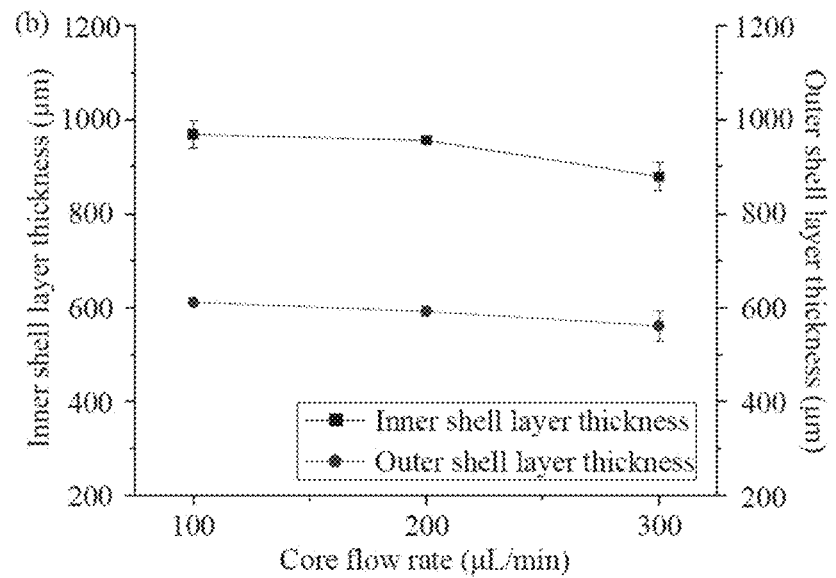

The effects of core, annular, and sheath flow rates on the dimensions of fabricated capsules are illustrated herein in terms of overall capsule and core diameters as well as the thickness of each shell layer. In particular, the effects of core flow rate on the geometry of double-layered capsules can be examined by fixing the annular and sheath flow rates at 800 μL/min and 1600 μL/min, respectively, while varying the core flow rate in the range of 100-300 μL/min. The geometries of fabricated double-layered capsules are measured, and their dimensions are shown in FIGS. 6A and 6B. As seen from FIG. 6A, both capsule and core diameters can increase with increasing core flow rate. Since the annular and sheath flow rates remain the same, the resulting volumes being dispensed do not vary. As such, the increased core diameter can cause a slight reduction of both inner and outer shell layer thicknesses as shown in FIG. 6B.

Figure 6C:
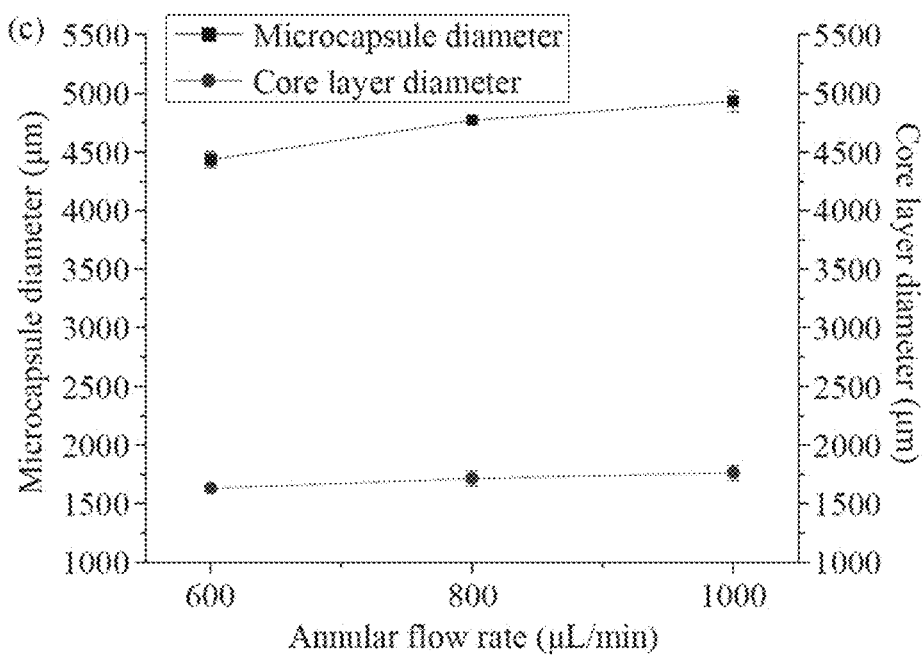
Figure 6D:
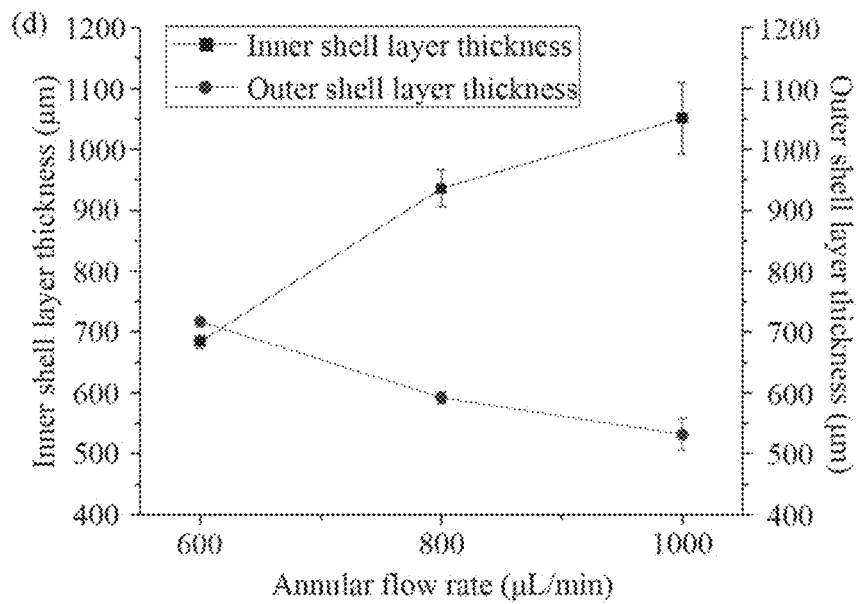

The effects of annular flow rate on the geometry of double-layered capsules can be examined by fixing the core and sheath flow rates at 200 μL/min and 1600 μL/min, respectively, while varying the annular flow rate in the range of 600-1000 μL/min. The geometries of fabricated double-layered capsules can be measured, and their dimensions are shown in FIGS. 6C and 6D. As seen in FIG. 6C, with increasing annular flow rate, the capsule diameter can also increase. Since the core and sheath flow rates remain the same, the resulting volumes being dispensed can change. Thus, the core diameter may not change (FIG. 6C). However, as seen in FIG. 6D, the increasing annular flow rate can increase the inner shell layer thickness, resulting in an increase in overall capsule diameter (FIG. 6C) and a reduction of outer shell layer thickness.

Figure 6E:
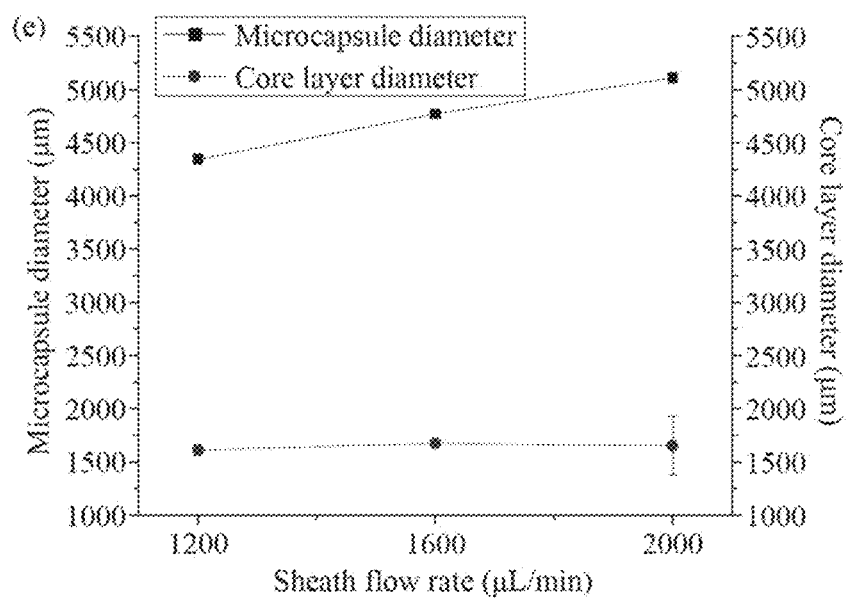
Figure 6F:
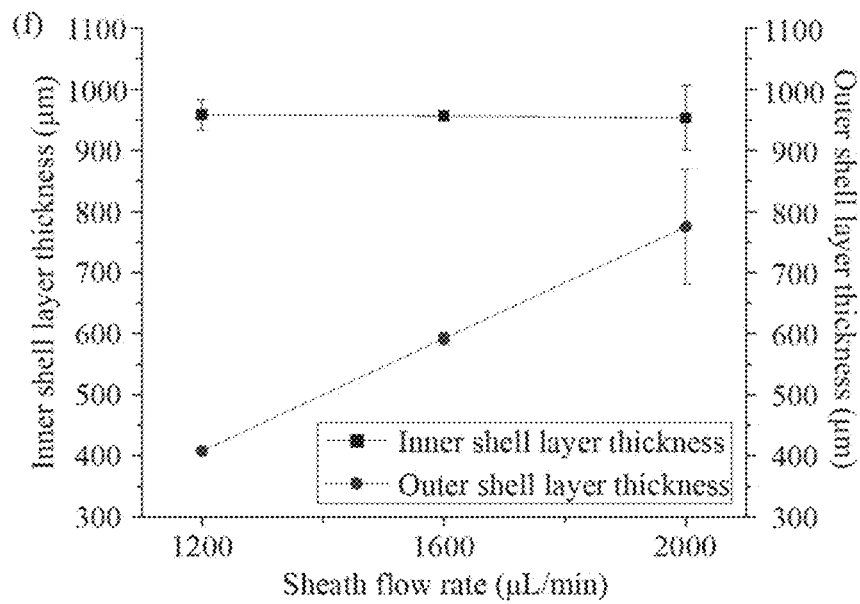

The effects of sheath flow rate on the geometry of double-layered capsules can be examined by fixing core and annular flow rates at 200 μL/min and 800 μL/min, respectively, while increasing the sheath flow rate from 1200 μL/min to 1600 μL/min to 2000 μL/min. The geometries of fabricated double-layered capsules are measured, and their dimensions are shown in FIGS. 6E and 6F. As seen in FIG. 6E, the increase of sheath flow rate can cause the increase of fabricated capsule diameter. Since the core and annular flow rates remain the same, the resulting volumes being dispensed can also be the same. As such, both the core diameter (FIG. 6E) and the inner shell layer thickness (FIG. 6F) can change while the outer shell layer thickness can increase (FIG. 6F).

As described herein, the selection of the flow rate ranges can be based on experimental observations, and fabrication processes can be numerically modeled and validated as a function of operating conditions for controlled fabrication of capsules with specific dimensions. In addition, capsule size of embodiments fabricated herein is around 1500 μm (millimeter scale) in diameter. For some applications such as controlled drug delivery, micro-scale capsules are desirable, and other multi-layered coaxial nozzle set with smaller channel dimensions can be designed and manufactured.

5. Conclusions

Embodiments of a three-layered coaxial nozzle fabrication system is described herein. Nozzles and capsule fabrication systems as described herein can be configured to fabricate double-layered capsules. To facilitate the droplet formation process, a vibrator can be integrated into the fabrication system to provide necessary perturbation for effective breakup of the fluid flow into droplets. Using numerical simulations, orthogonal experiments can be conducted to optimize the structure of the coaxial nozzle for capsule fabrication, and such nozzles and systems can be fabricated. Using sodium alginate solutions as the model liquid material for inner and outer shell layers and calcium chloride solution as the core fluid, multi-layered, such as double-layered capsules can be fabricated. Some conclusions from the disclosure as described herein can be drawn as follows:

1. Double-layered alginate capsules can be successfully fabricated using embodiments of three-layered coaxial nozzles and capsule fabrication systems comprising such; and
2. Operating conditions (core, annular, and sheath flow rates) can affect the dimensions of fabricated double-layered capsules. Increasing core flow rate can lead to increasing capsule and core diameters while the inner and outer shell layer thicknesses can decrease. Increasing annular flow rate can result in increased capsule diameter and inner shell layer thickness while the outer shell layer thickness can decrease. Increasing sheath flow rate can lead to increased capsule diameter and outer shell layer thickness but may have little effect on the core diameter and inner shell layer thickness.

Additional design and simulation results of orthogonal experiments for embodiments of systems and methods are shown in FIG. 23, where $X_i$ illustrates the variable X at the $i^{th}$ setting, (variable X=A, B, C and D as defined in FIG. 8 (Table 2) and i=1, 2, and 3 which depicts three different values of the corresponding X), SD is the standard deviation of the velocity which is used to assess the velocity uniformity of the annular and sheath flows at the nozzle outlet location, $T_{iX}$ illustrates the sum of the $i^{th}$ setting of variable X in different designs and $T_{iX}=\Sigma SD_{iX}$, $t_{iX}$ is the average value of $T_{iX}$, and $R_X$ is the range of the $X^{th}$ column and $R_X=Max(t_{1X}, t_{2X}, t_{3X})-Min(t_{1X}, t_{2X}, t_{3X})$. Herein, $R_X$ is used to assess the sensitivity of velocity uniformity to different structure dimensions. From the range analysis as shown in FIG. 23, the effects of different structure dimensions on the uniformity of the velocity field is evaluated. Specifically, for the annular channel since $R_A>R_B>R_C>R_D$, the inner diameter of the channel influences the velocity uniformity more significantly than the other dimensions; for the sheath channel since $R_C>R_A>R_B>R_D$, the compression angle influences the velocity uniformity more significantly than the other dimensions. When determining the nozzle dimensions, these key dimensions must be guaranteed first before optimizing the other dimensions in order to have an optimized three-layered coaxial nozzle.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5.0%" should be interpreted to include not only the explicitly recited concentration of about 0.1 wt % to about 5.0 wt %, but also include individual concentrations (e.g., 1.0%, 2.0%, 3.0%, and 4.0%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim:

1. A capsule fabrication system comprising:
    a coaxial nozzle comprising a core channel, an annular channel, and a sheath channel, the coaxial nozzle configured to form a compound flow of at least one fluid, wherein the annular channel and the sheath channel are configured to increase uniformity of velocity of distribution of fluid flow at an annular channel outlet and a sheath channel outlet of the coaxial nozzle,
    wherein the annular channel has a diameter of about 8.5 mm, a first length of between about 2.0 mm and about 4.0 mm, a second length of between about 12.5 mm and about 13.0 mm, and a height between about 2.0 mm and about 2.5 mm, and
    wherein the sheath channel has a length between about 1.5 mm and about 2.0 mm, a first diameter between about 14.0 mm and about 16.0 mm, a second diameter between about 11.0 mm and about 13.0 mm, and a height between about 8.0 mm and about 8.6 mm, the capsule fabrication system further comprising:
    a fluid delivery system configured to deliver a first fluid of the at least one fluid to the core channel, a second fluid of the at least one fluid to the annular channel, and a third fluid of the at least one fluid to the sheath channel, wherein the compound flow comprises at least one of: a core flow of the first fluid, an annular flow of the second fluid, and a sheath flow of the third fluid;
    a vibrator configured to introduce a vibration to the compound flow to form one or more capsules; and
    a collection bath configured to receive one or more capsules from the coaxial nozzle.

2. The capsule fabrication system of claim 1, wherein at least one of: the first fluid, the second fluid, or the third fluid comprises alginate.

3. The capsule fabrication system of claim 1, wherein at least one of: the first fluid, the second fluid, or the third fluid comprises $CaCl_2$.

4. The capsule fabrication system of claim 1, wherein the first fluid is different from the second fluid, the third fluid, or both.

5. The capsule fabrication system of claim 1, wherein the coaxial nozzle further comprises:
    a core inlet configured to deliver a first fluid to the core channel,
    an annular inlet configured to deliver a second fluid to the annular channel, and a sheath inlet configured to deliver a third fluid to the sheath channel.

6. The capsule fabrication system of claim 1, wherein the one or more capsules are generated by an ultrasonic vibration applied to the coaxial nozzle during dripping.

7. The capsule fabrication system of claim 6, wherein the ultrasonic vibration is applied at a given frequency and amplitude configured to facilitate breakup of fluid flows and form multi-layered capsules.

8. The capsule fabrication system of claim 1, wherein the one or more capsules are formed in air.

9. The capsule fabrication system of claim 1, wherein the collection bath comprises a crosslinking agent configured to stabilize the one or more capsules introduced into the collection bath.

10. The capsule fabrication system of claim 9, wherein the crosslinking agent comprises $Ca^{2+}$.

11. The capsule fabrication system of claim 1, wherein the one or more capsules one or more multi-layered capsules.

12. The capsule fabrication system of claim 1, wherein the one or more capsules comprise one or more multi-layered capsules having a core-shell-shell structure.

13. The capsule fabrication system of claim 1, wherein the coaxial nozzle comprises:
   an inner set comprising a first center opening forming the core channel;
   a middle set comprising a second center opening configured to receive the inner set forming the annular channel between at least a portion of the inner set and the middle set, the middle set configured to support and hold the inner set; and
   an outer set comprising a third center opening configured to receive the middle set forming the sheath channel between at least a portion of the middle set and the outer set.

14. The capsule fabrication system of claim 1, wherein the coaxial nozzle comprises one or more outlet nozzles.

15. A capsule fabrication system comprising:
   a coaxial nozzle, wherein the coaxial nozzle comprises a core channel, an annular channel, and a sheath channel, and wherein the coaxial nozzle is configured to output one or more capsules, wherein the coaxial nozzle is dimensioned and configured to increase uniformity of velocity of distribution of fluid flow at an annular channel outlet and a sheath channel outlet of the coaxial nozzle,
   wherein the annular channel has a diameter of about 8.5 mm, a first length of between about 2.0 mm and about 4.0 mm, a second length of between about 12.5 mm and about 13.0 mm, and a height between about 2.0 mm and about 2.5 mm, and
   wherein the sheath channel has a length between about 1.5 mm and about 2.0 mm, a first diameter between about 14.0 mm and about 16.0 mm, a second diameter between about 11.0 mm and about 13.0 mm, and a height between about 8.0 mm and about 8.6 mm,
   wherein the capsule fabrication system further comprises:
   a collection bath configured to receive one or more capsules from the coaxial nozzle.

16. The capsule fabrication system of claim 15, further comprising:
   a vibrator attached to or in physical communication with the coaxial nozzle.

17. The capsule fabrication system of claim 15, further comprising:
   a fluid delivery system configured to deliver fluid to one or more of the core channel, the annular channel, and the sheath channel.

18. The capsule fabrication system of claim 15, wherein the one or more capsules comprise one or more multi-layered capsules.

19. The capsule fabrication system of claim 15, wherein the collection bath comprises a crosslinking agent configured to crosslink the one or more capsules to form one or more stabilized capsules.

* * * * *